(12) United States Patent
Dai et al.

(10) Patent No.: US 11,903,931 B2
(45) Date of Patent: Feb. 20, 2024

(54) SALTS OF SELECTIVE ESTROGEN RECEPTOR DEGRADERS

(71) Applicant: InventisBio Co., Ltd., Shanghai (CN)

(72) Inventors: Xing Dai, Short Hills, NJ (US);
Yueheng Jiang, Belmont, MA (US)

(73) Assignee: INVENTISBIO CO., LTD., Shanghai (CN)

( * ) Notice: Subject to any disclaimer, the term of this patent is extended or adjusted under 35 U.S.C. 154(b) by 138 days.

(21) Appl. No.: 17/568,324

(22) Filed: Jan. 4, 2022

(65) Prior Publication Data

US 2022/0202790 A1   Jun. 30, 2022

Related U.S. Application Data

(63) Continuation of application No. 16/796,448, filed on Feb. 20, 2020, now Pat. No. 11,241,418.

(30) Foreign Application Priority Data

Dec. 24, 2018   (WO) ................ PCT/CN2018/123031

(51) Int. Cl.
| | |
|---|---|
| *C07D 471/04* | (2006.01) |
| *A61K 31/437* | (2006.01) |
| *A61K 31/4375* | (2006.01) |
| *A61K 45/06* | (2006.01) |

(52) U.S. Cl.
CPC .......... *A61K 31/4375* (2013.01); *A61K 45/06* (2013.01); *C07D 471/04* (2013.01); *C07B 2200/13* (2013.01)

(58) Field of Classification Search
CPC ...... C07D 471/04; A61K 31/437; A61P 35/00
USPC ............................................ 546/85; 514/292
See application file for complete search history.

(56) References Cited

U.S. PATENT DOCUMENTS

| | | | |
|---|---|---|---|
| 10,647,724 | B2 | 5/2020 | Dai |
| 11,241,418 | B2 * | 2/2022 | Dai ...................... C07D 471/04 |
| 2014/0357661 | A1 | 12/2014 | Bradbury et al. |

FOREIGN PATENT DOCUMENTS

| | | |
|---|---|---|
| CN | 106488767 A | 3/2017 |
| CN | 105229004 B | 5/2017 |
| JP | 2016522835 | 8/2016 |
| WO | 2014191726 | 12/2014 |
| WO | 2016/027285 A2 | 2/2016 |
| WO | 2017/059139 A1 | 4/2017 |
| WO | 2017/136688 A1 | 8/2017 |
| WO | 2018/130123 A1 | 7/2018 |
| WO | 2018/130124 A1 | 7/2018 |
| WO | 2020/132785 A1 | 7/2020 |

OTHER PUBLICATIONS

Extended European Search Report issued in corresponding European Application No. 18945105.7 dated May 24, 2022, 15 pages.
Bastin, Richard J., et al., "Salt Selection and Optimisation Procedures for Pharmaceutical New Chemical Entities", Organic Process Research & Development, Jul. 19, 2000, vol. 4, No. 5, pp. 427-435.
Written Opinion of the International Searching Authority for PCT Application No. PCT/CN2018/123031 dated Sep. 26, 2019, 6 pages.
International Search Report for PCT Application No. PCT/CN2018/123031 dated Sep. 26, 2019, 4 pages.
Fang et al., "Pharmaceutics . . . ", China Medical Science and Technology Press, Mar. 31, 2016, pp. 35-37—See ISR for relevancy.
Makoto Ono, Journal of Pharmaceutical Science and Technology, Japan, 2013, vol. 73, No. 3, 8 pages.
Bastin, et al., "Salt Selection and Optimisation Procedures for Pharmaceutical New Chemical Entities ", Organic Process Research & Development, 2000, vol. 4, No. 5, 9 pages.

* cited by examiner

*Primary Examiner* — Charanjit Aulakh
(74) *Attorney, Agent, or Firm* — Nixon & Vanderhye, P.C.

(57) ABSTRACT

Provided herein are compounds, salts, crystalline forms, and pharmaceutical compositions that are related to Selective Estrogen Receptor Degraders, as well as methods of preparing the same. Also provided herein are methods of using the compounds, salts, crystalline forms, and pharmaceutical compositions for the treatment of diseases or disorders, such as breast cancer.

12 Claims, 18 Drawing Sheets

SALTS OF SELECTIVE ESTROGEN RECEPTOR DEGRADERS

CROSS REFERENCE TO RELATED APPLICATIONS

This application is a continuation of U.S. application Ser. No. 16/796,448, filed Feb. 20, 2020, which claims priority to International Application No. PCT/CN2018/123031, filed Dec. 24, 2018, the content of each of which is incorporated herein by reference in its entirety.

BACKGROUND OF THE INVENTION

Field of the Invention

In various embodiments, the present invention generally relates to novel salts of Selective Estrogen Receptor Degraders (SERDs), pharmaceutical compositions comprising the same, and methods of preparation and use thereof.

Background Art

Breast cancer is the most common cause of death for women worldwide. Majority of breast cancer (~80%) depends on the signaling pathway mediated by the estrogen receptor (ER) for growth. Therefore, targeting the ER or its signaling pathway remains to be the key in development of drug for treating breast cancer. Estrogen receptors (including ERα and ERβ) are a group of receptors that are activated by the hormone estrogen (17β-estradiol). Current therapy for ER positive (ER+) breast cancer including agents that inhibit the ER activity through direct binding to the ligand binding domain of the receptor (e.g., tamoxifen); blocking the synthesis of estrogen (e.g., aromatase inhibitor such as anastrozole and letrozole); or inducing the degradation of ER (e.g., fulvestrant).

Drugs that inhibit estrogen receptor or block the production of estrogens are commonly used in the treatment and management of ER+ breast cancer and other hormone-dependent cancers. However, drug resistance remains a challenge in breast cancer treatment, particularly treatment of cancers in advanced stages.

BRIEF SUMMARY OF THE INVENTION

Selective Estrogen Receptor Degraders (SERD) are a class of small molecules that bind to the estrogen receptor, resulting in degradation of the estrogen receptor. Studies showed that SERDs are specifically useful in treating cancers that are resistant to other drugs such as tamoxifen and/or aromatase inhibitors (McDonnell et al., J. Med. Chem. 2015, 58, 4883-4887). Fulvestrant is a SERD that has been approved for treatment of ER+ breast cancer. However, fulvestrant is metabolized quickly and is administered by intramuscular injection monthly, which limit the effective degradation of ER (~50% ER degradation in clinical samples) compared to the complete ER degradation seen in in vitro study. Recently, ER mutations have been detected in biopsy samples from breast cancer patients who have developed resistance to treatment of aromatase inhibitor. These mutations are mostly frequently occurring at amino acid 537 and 538 within the ligand binding domain of ER. Interestingly, these mutated ERs still bind to and are inhibited by both tamoxifen and fulvestrant to some degree (Li et al., 2013 Cell Reports 4, 1116-1130; Toy et al., 2013, 45, 1439-1445; Robinson et al., Nature Genetics 2013, 45, 1446-1451). It has also been shown that fulvestrant can still effectively degrade the mutated Try537Ser ER protein. Compounds targeting the ER degradation similar to fulvestrant could effectively degrade the mutated ER protein as well and are useful in treating breast cancer patients that developed resistance to aromatase inhibitor.

WO2017/136688 describes various SERDs as useful for treating various diseases or disorders such as breast cancer, in particular ER+ breast cancer, and/or other ER related diseases. In various embodiments, the present invention is directed to certain salts of SERDs, for example, in a crystalline form and/or as a substantially pure isolated salt, pharmaceutical compositions comprising the same, methods of preparing the same, and methods of using the same.

Certain specific embodiments of the present invention are directed to amine salts of (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid ("Compound FA"). In some embodiments, the amine salt is a meglumine salt, trialkyl amine salt, lysine salt, arginine salt, tromethamine salt, choline salt, or ammonium salt.

In some embodiments, the present disclosure provides a meglumine salt of Compound FA. In some embodiments, the meglumine salt of Compound FA can be in the form of Form I, II, or III as defined herein.

In some embodiments, the present disclosure provides a lysine salt of Compound FA. In some embodiments, the lysine salt of Compound FA is an L-lysine salt (1:1 molar ratio). In some embodiments, the L-lysine salt can be in the form of Form A as defined herein.

In some embodiments, the present disclosure provides a trialkyl amine salt of Compound FA, such as diisopropylethyl amine salt. In some embodiments, the trialkylamine salt is in a crystalline form.

In some embodiments, the present disclosure provides a tromethamine salt of Compound FA. In some embodiments, the tromethamine salt can be in a crystalline form. In some embodiments, the present disclosure provides a choline salt of Compound FA. In some embodiments, the choline salt can be in a crystalline form.

In some embodiments, the present disclosure also provides methods for preparing the amine salts of Compound FA. Typically, the method comprises dissolving Compound FA in a suitable solvent to form a Compound FA solution and then adding appropriate amine into the solution.

Some embodiments of the present disclosure are also directed to a synthetic method of preparing Compound FA or a salt thereof. In some embodiments, the method comprises reacting a tryptamine compound (described herein), or a salt thereof, with an aldehyde compound (described herein), or a salt thereof, under suitable conditions (e.g., heating in toluene) to form Compound FA or a salt thereof. In some embodiments, the method further comprises converting the Compound FA or salt thereof into an amine salt of Compound FA (e.g., as described herein).

The salts of the present disclosure, such as the amine salts herein (e.g., any of the crystalline forms described herein) can be included in a pharmaceutical composition, for example, for the treatment of a proliferative disease or disorder such as breast cancer, in particular ER+ breast cancer, and/or diseases or disorders associated with ER. In some embodiments, the pharmaceutical composition can comprise a therapeutically effective amount of any one or more of the salts of the present disclosure. For example, in some specific embodiments, the active ingredient in the pharmaceutical composition can comprise, consist essentially of, or consist of the meglumine salt of Compound FA in Form I. In some specific embodiments, the active ingredient in the pharmaceutical composition can comprise, consist essentially of, or consist of the meglumine salt of Compound FA in Form II. In some specific embodiments, the active ingredient in the pharmaceutical composition can comprise, consist essentially of, or consist of the meglumine salt of Compound FA in Form III. In some specific embodiments, the active ingredient in the pharmaceutical composition can comprise, consist essentially of, or consist of the meglumine salt of Compound FA in Form I, amorphous form, or a mixture thereof. The salts herein, such as the amine salts herein (e.g., any of the crystalline forms described herein) can be used alone, in combination with each other, or with an additional pharmaceutical agent, e.g., described herein.

The pharmaceutical compositions described herein can be formulated for any suitable routes of administration. In some embodiments, the pharmaceutical composition can be formulated for oral administration. For example, in some embodiments, the pharmaceutical composition can be a tablet or a capsule.

Certain embodiments of the present invention are directed to methods of using the salts of the present disclosure, such as the amine salts herein (e.g., any of the crystalline forms described herein) and/or pharmaceutical compositions herein for treating diseases or disorders associated with ER, such as ER positive breast cancer or a gynecological disease associated with ER. The methods described herein are not limited to any specific routes of administration. For example, in some embodiments, the administration can be oral administration. In some embodiments, the methods herein can further include administering an additional pharmaceutical agent (e.g., described herein) to the subject in need thereof. In some embodiments, the additional pharmaceutical agent can be administered concurrently or sequentially in any order.

BRIEF DESCRIPTION OF THE DRAWINGS/FIGURES

FIG. 1A shows a representative X-ray powder diffraction (XRPD) spectrum of crystalline form I of the meglumine salt of Compound FA. FIG. 1B shows a representative thermogravimetric analysis (TGA) and differential scanning calorimetry (DSC) analysis of crystalline form I of the meglumine salt of Compound FA. FIG. 1C presents XRPD spectra showing that Form I remained unchanged after storage under the condition of 25° C./92.5% RH for 10 days.

Figure 5A:
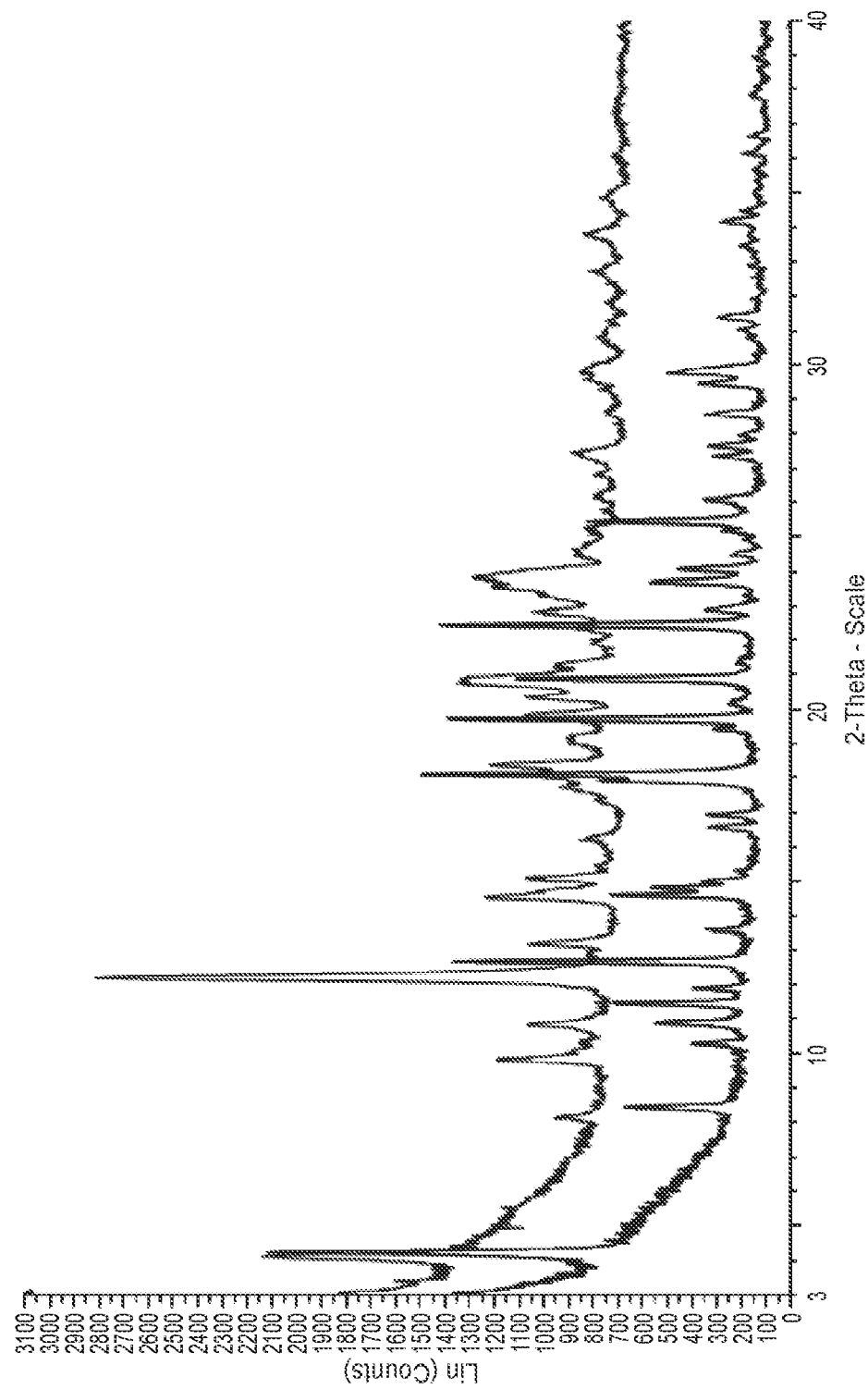
Figure 5B:
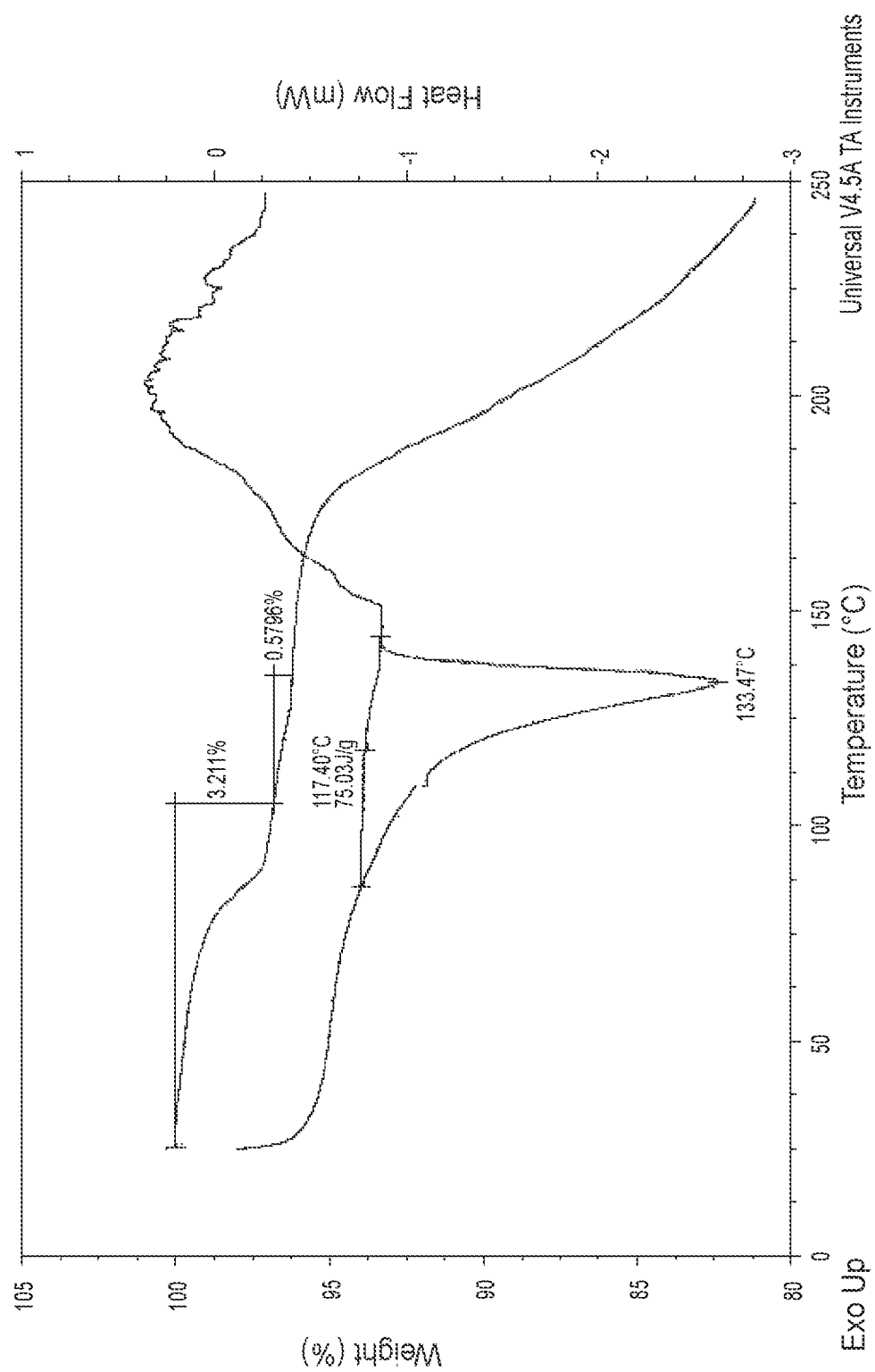
Figure 5C:
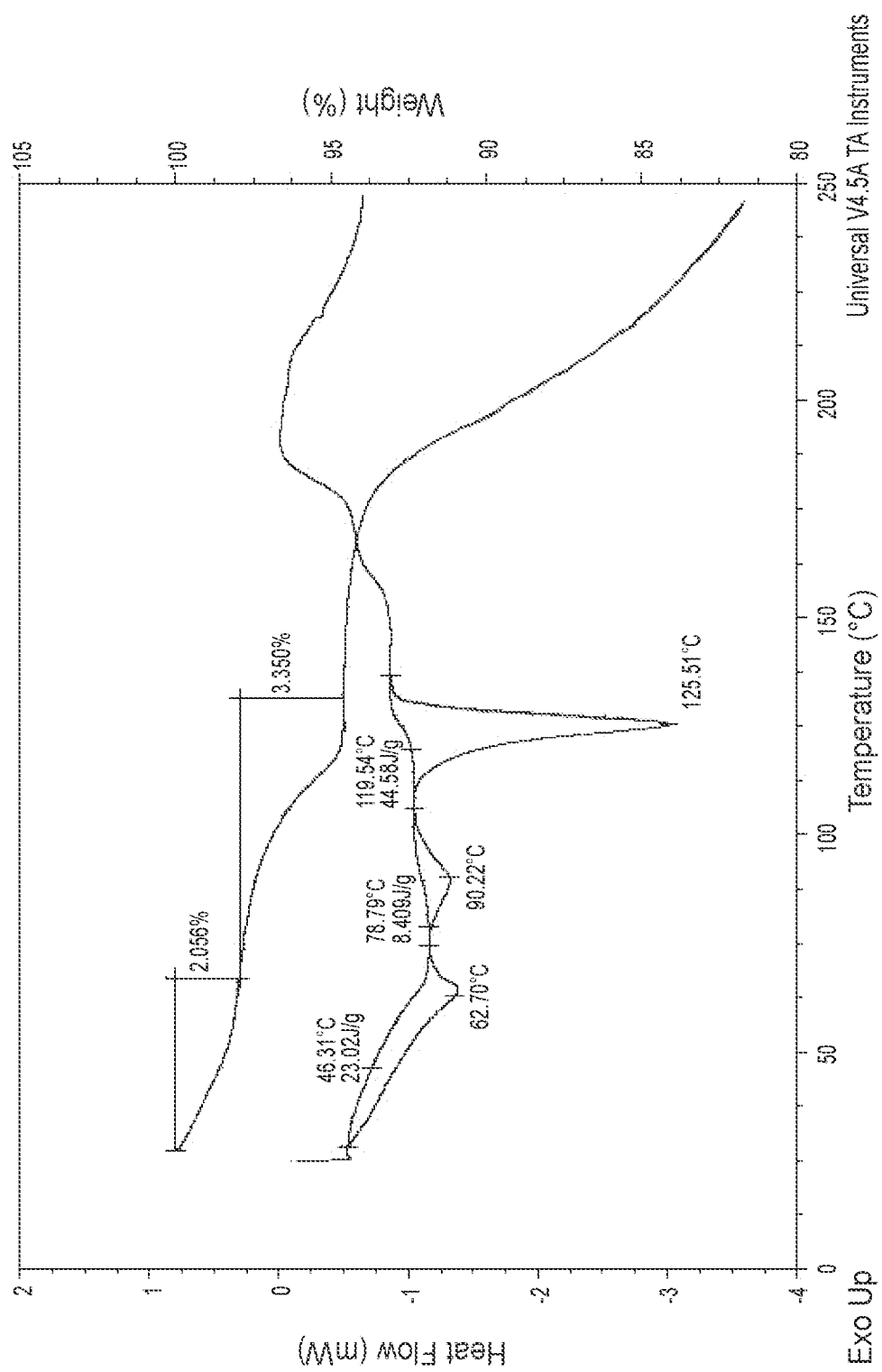

FIG. 5A shows representative XRPD spectra of crystalline forms of the tromethamine salt of Compound FA (1:1 molar ratio). A representative XRPD spectrum of tromethamine salt obtained from first condition (methanol as solvent) in Example 8 is shown on the bottom. A representative XRPD spectrum of tromethamine salt obtained from the second condition (acetonitrile/water as solvent) in Example 8 is shown on the top. FIG. 5B shows a representative TGA and DSC analysis of the crystalline form obtained from the first condition. FIG. 5C shows a representative TGA and DSC analysis of the crystalline form obtained from the second condition.

Figure 6A:
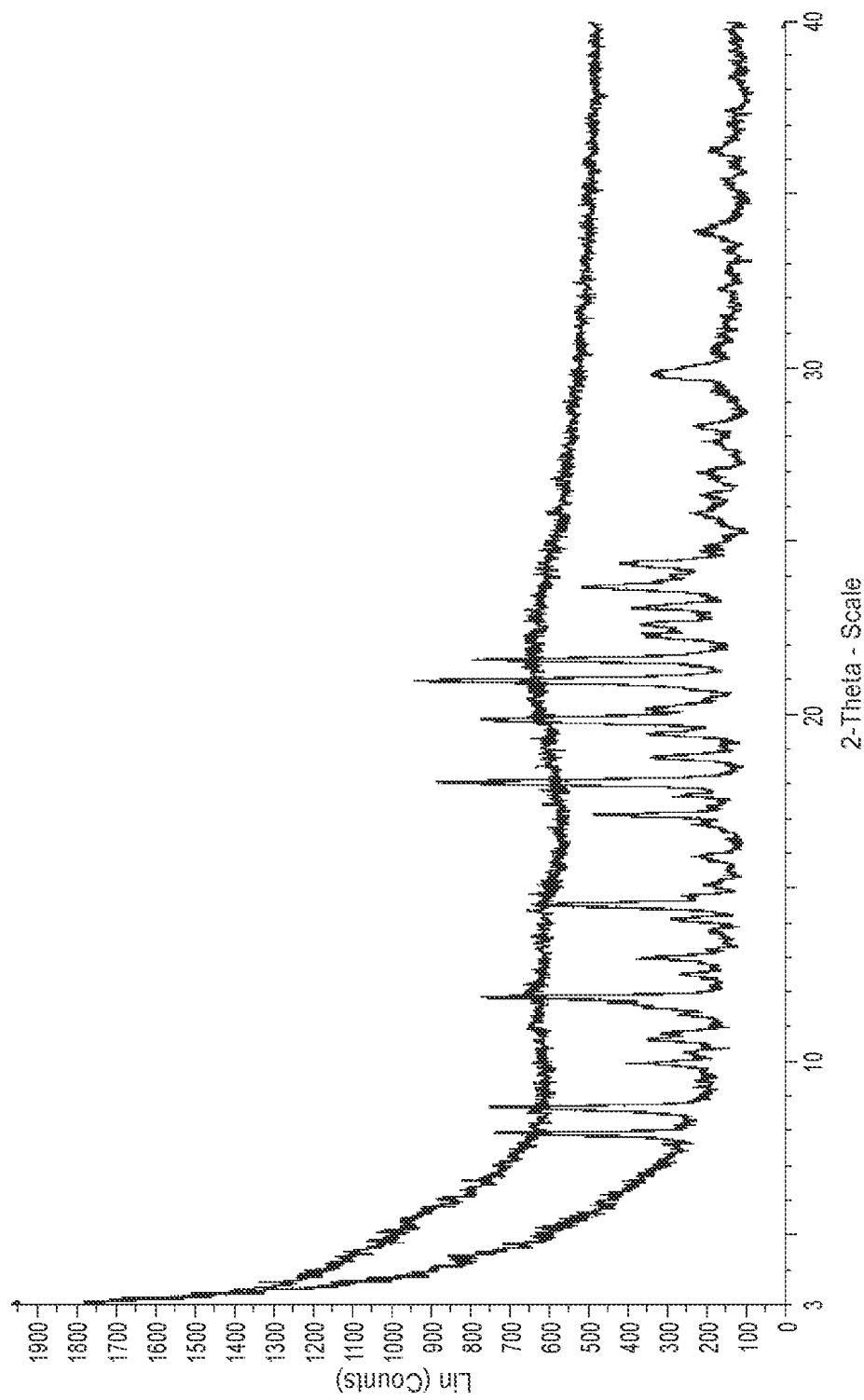
Figure 6B:
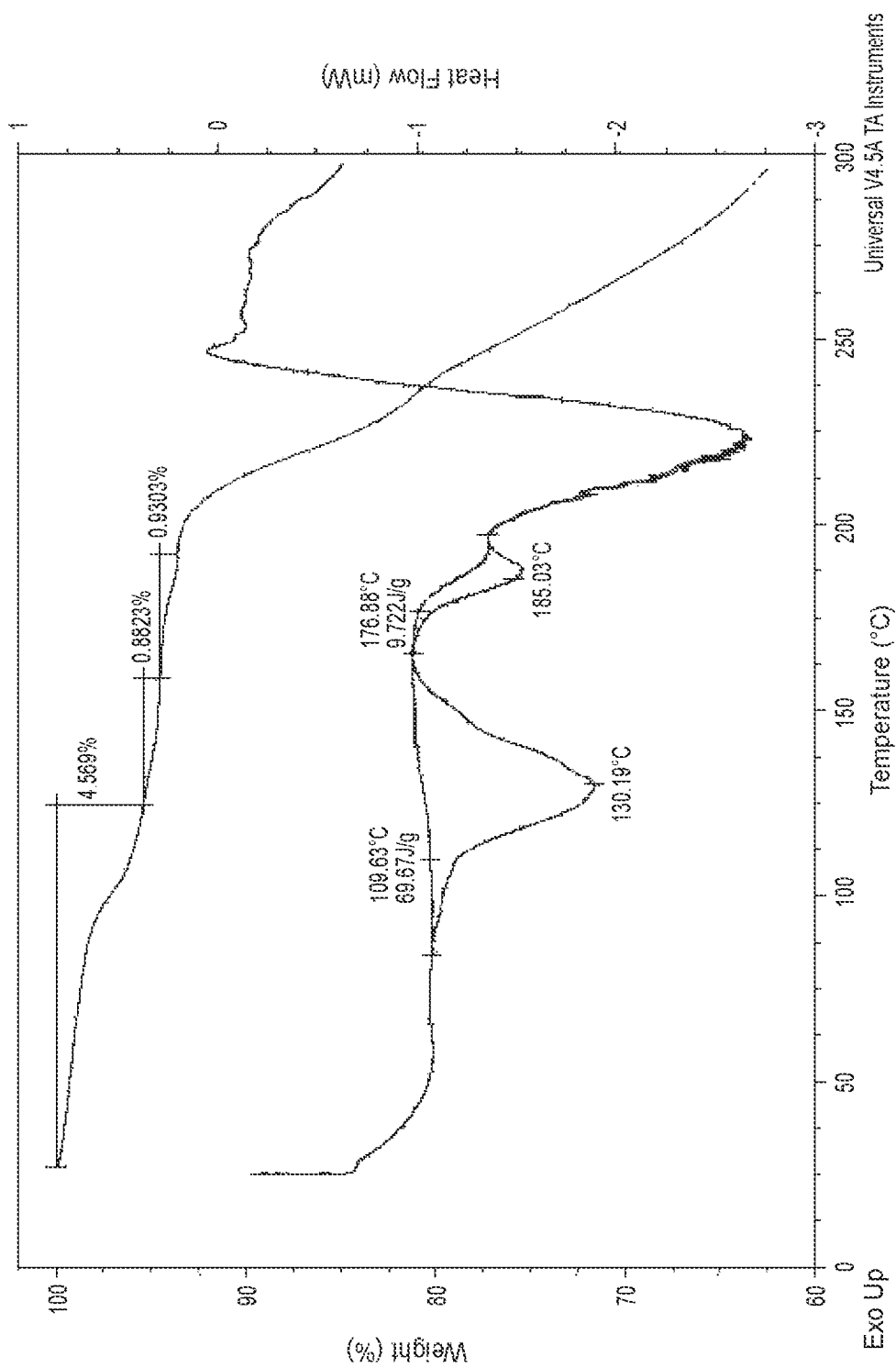

FIG. 6A shows representative XRPD spectra of solid forms of the choline salt of Compound FA (1:1 molar ratio). A representative XRPD spectrum of the choline salt obtained from the MTBE (methyl tert-butyl ether) procedure in Example 9, which is amorphous, is shown on the top. A representative XRPD spectrum of the choline salt obtained from the acetonitrile procedure in Example 9, which is crystalline, is shown on the bottom. FIG. 6B shows a representative TGA and DSC analysis of the crystalline form obtained from the acetonitrile procedure.

Figure 7A:
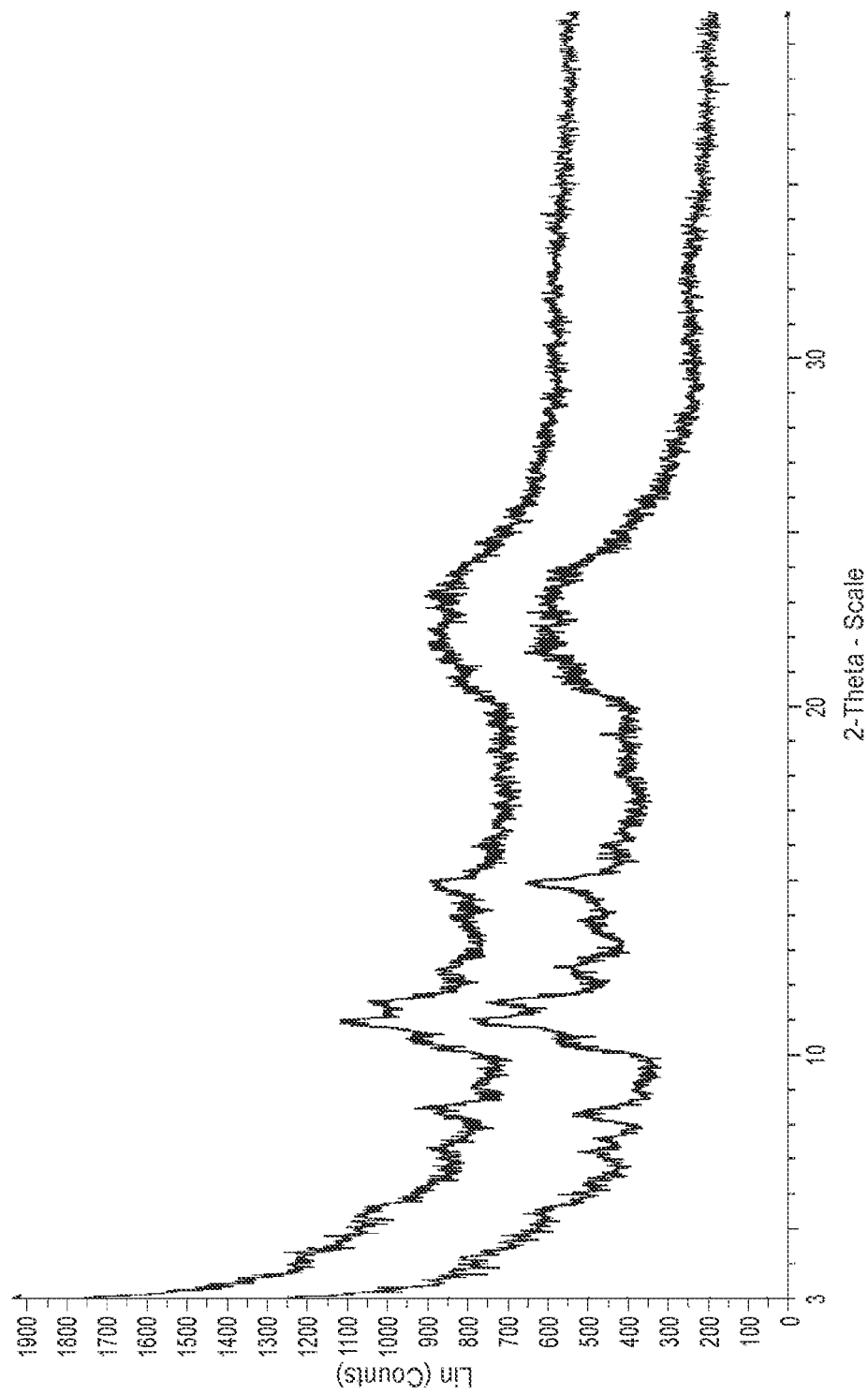
Figure 7B:
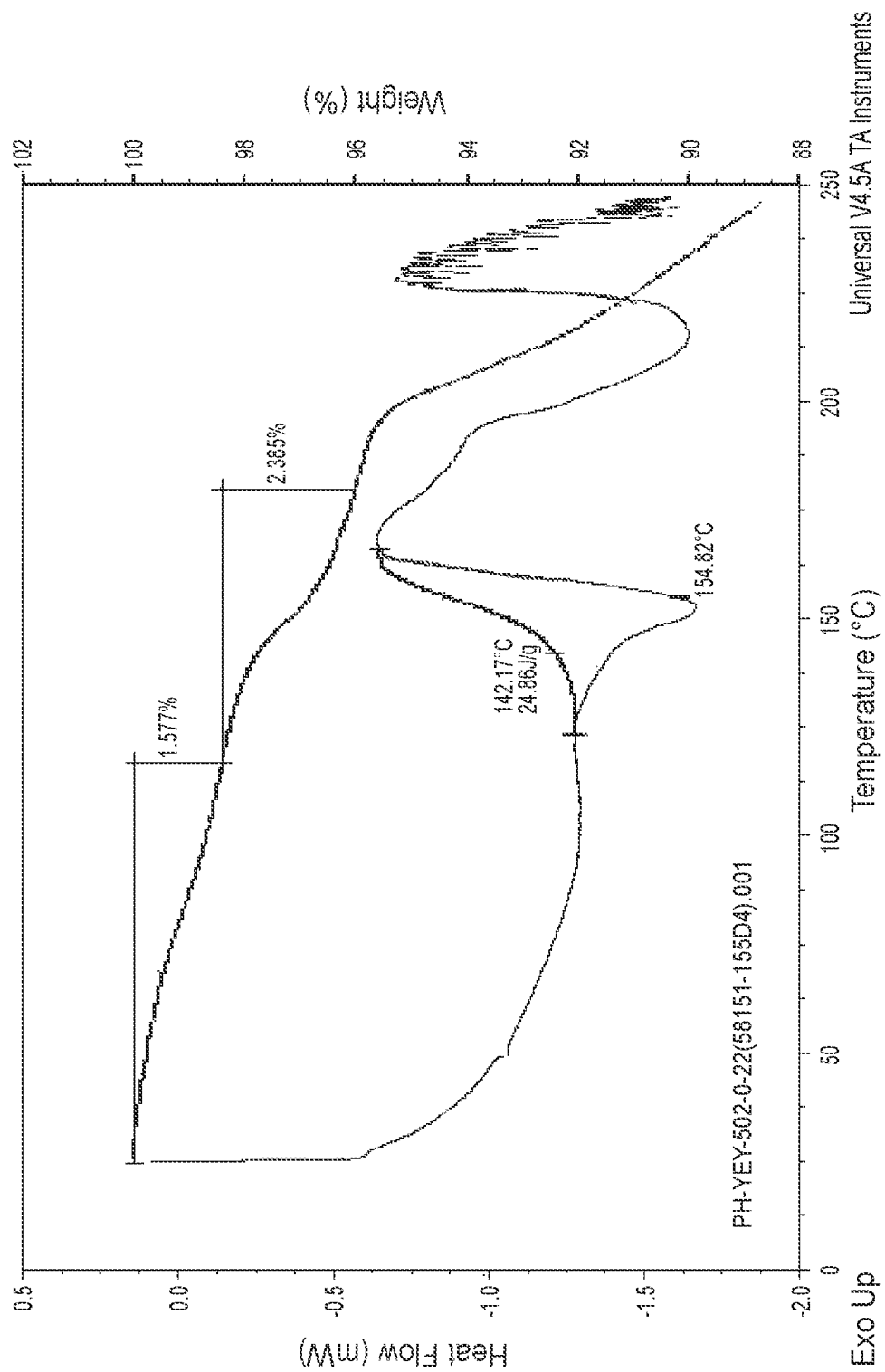

FIG. 7A shows representative XRPD spectra of a solid form of the free acid Compound FA, before (lower trace) and after (top trace) Dynamic moisture sorption analysis (DVS) studies. FIG. 7A shows that the solid form of the free acid did not change before and after the DVS studies, as evidenced by their XRPD spectra. FIG. 7B shows a representative DSC spectrum of the solid form of the free acid, Compound FA.

Figure 8A:
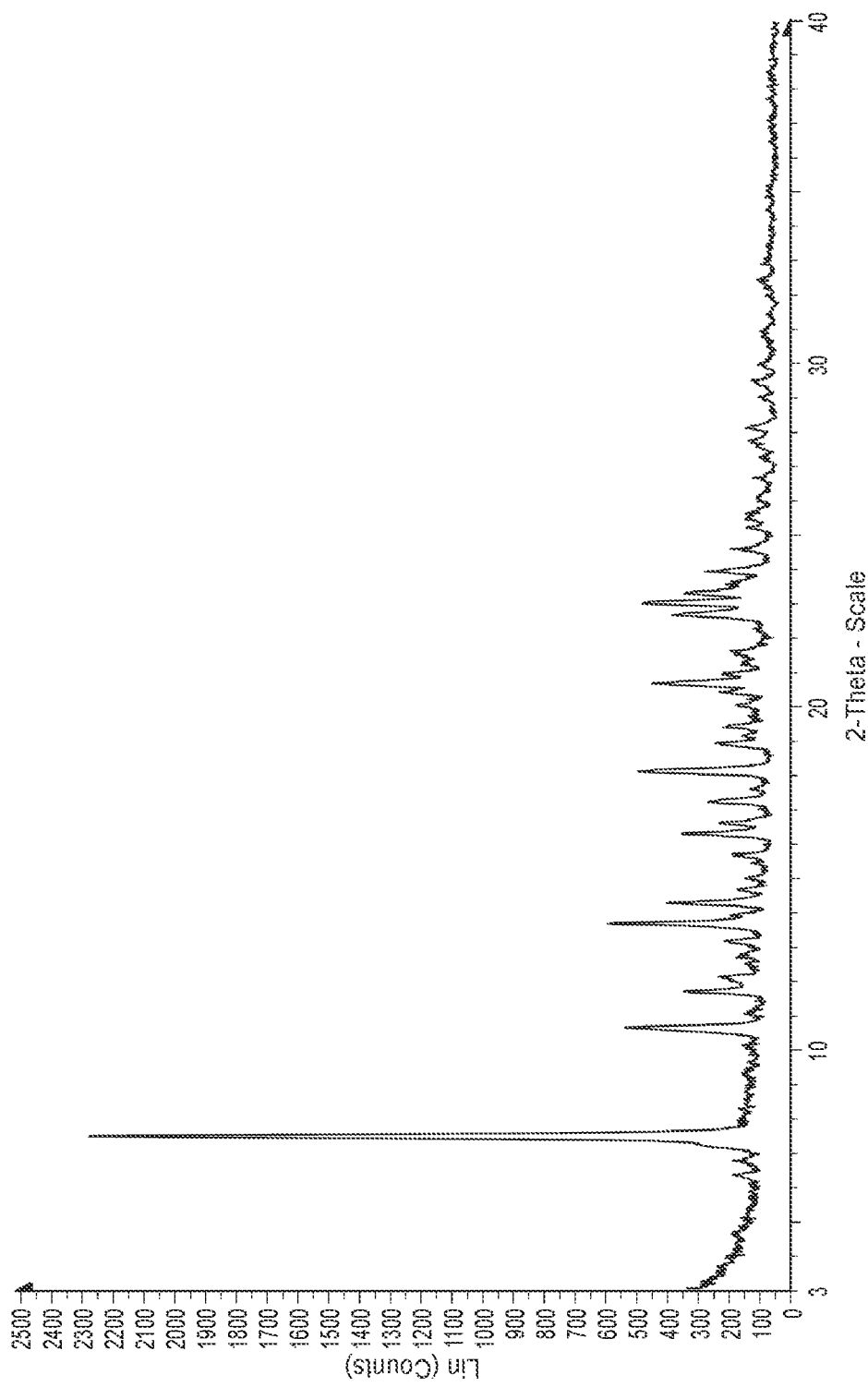
Figure 8B:
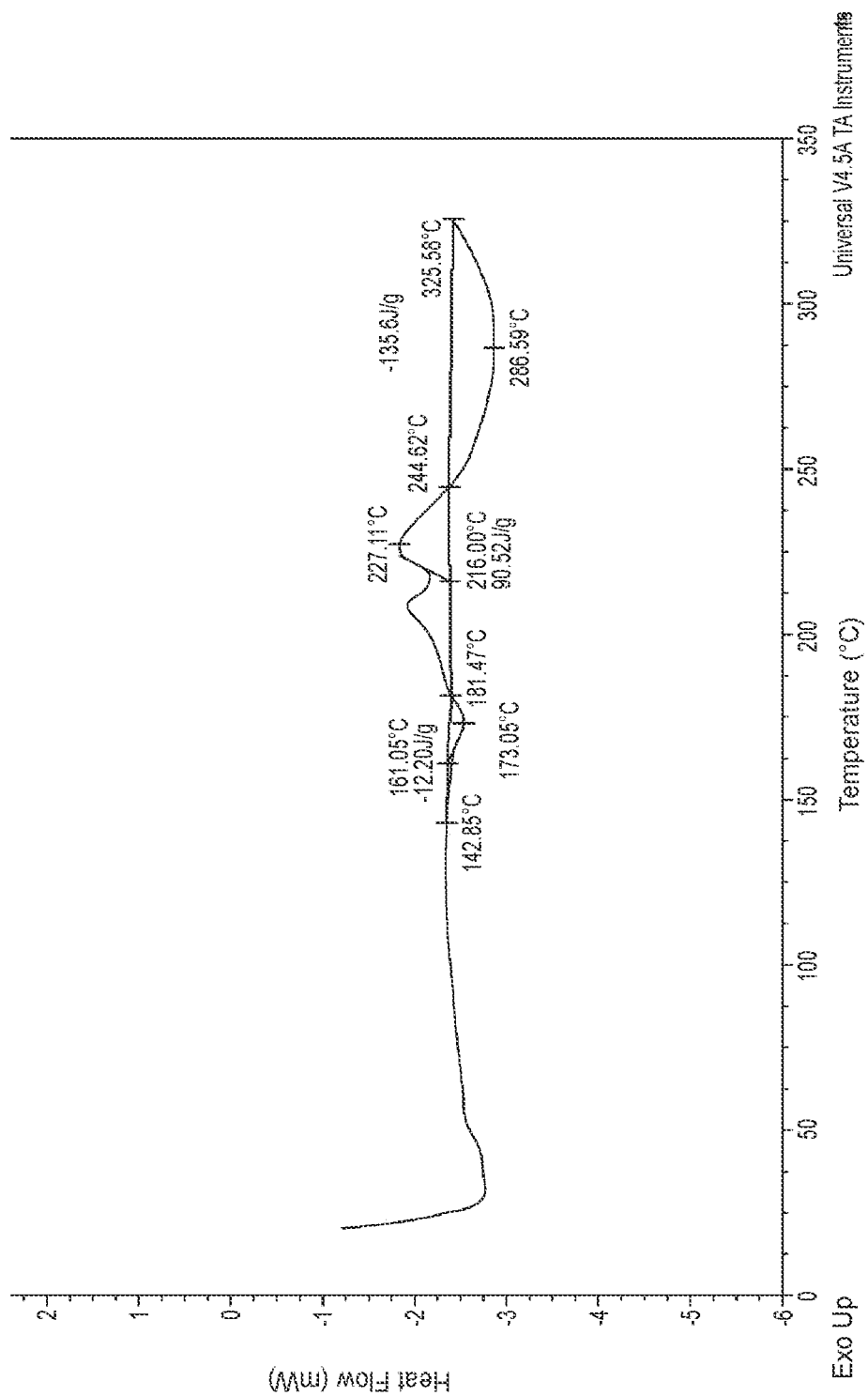

FIG. 8A shows a representative XRPD spectrum of a crystalline form of the diisopropylethyl amine salt of Compound FA (1:1 molar ratio) prepared in Example 2. FIG. 8B shows a representative DSC analysis of the crystalline form.

DETAILED DESCRIPTION OF THE INVENTION

In various embodiments, the present invention is directed to novel salts of SERDs. As discussed in details herein, the present inventors have found that Compound FA, (E)-3-(3, 5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid, can form salts with some bases, such as alkali or alkaline bases, and amine bases, but not with a variety of acids that were tested, such as HCl. Some of the salts, such as the amine salts, can also exist in a solid form, which can be a crystalline, solvate, hydrate, or amorphous form. These salts offer alternative ways for preparing, formulating, and using Compound FA. As exemplified in the Examples section, some representative salt forms with L-lysine and meglumine of Compound FA can exist in various crystalline forms, which can have enhanced solubility in water at both pH 1.2 and 6.8 and can have enhanced stability compared to Compound FA itself (i.e., the free acid form). Accordingly, in some embodiments, the salt forms herein can be more suited for various pharmaceutical uses compared to the free acid form.

Amine Salts

In various embodiments, the present invention is directed to an amine salt (e.g., pharmaceutically acceptable amine salt) of (E)-3-(3,5-dichloro-4-(1R,3R)-2-(2-fluoro-2-methylpropyl)-3-methyl-2,3,4,9-tetrahydro-1H-pyrido[3,4-b]indol-1-yl)phenyl)acrylic acid ("Compound FA"):

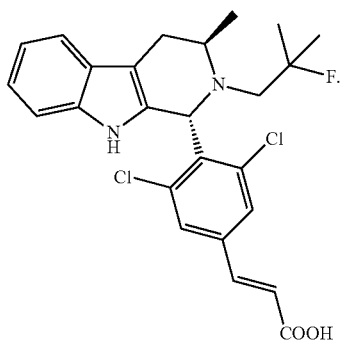

Compound FA

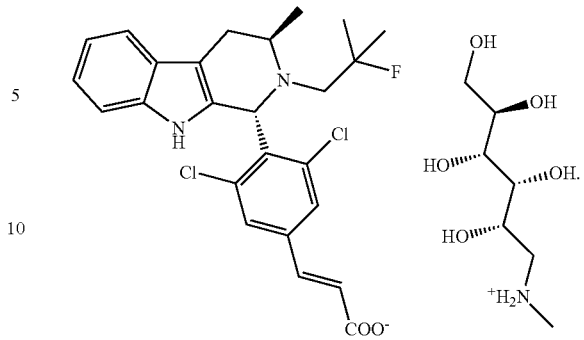

Compound FA can be referred to herein as in its free acid form to distinguish it from a salt formed with an external acid or base, even though internal ionization of the carboxylic acid function in Compound FA is theoretically possible.

Various amine salts are useful for the present disclosure. In some embodiments, the amine salt can be a meglumine salt, trialkyl amine salt, lysine salt, arginine salt, tromethamine salt, choline salt, or ammonium salt. Typically, the amine salt herein can exist in a solid form, such as in a crystalline form or an amorphous form, or a mixture thereof.

In some embodiments, the amine salt can be substantially pure. For example, in some embodiments, the amine salt of Compound FA (e.g., L-lysine salt or meglumine salt) is characterized by a purity by weight and/or by HPLC area of at least 70% (e.g., at least 75%, at least 80%, at least 85%, at least 90%, at least 95%, at least 97%, or at least 99%). In some embodiments, the amine salt of Compound FA (e.g., L-lysine salt or meglumine salt) is characterized by a purity by weight and/or by HPLC area of about 70%, about 75%, about 80%, about 85%, about 90%, about 95%, about 97%, about 99%, or any ranges between the specified values. Unless otherwise obvious from context, for the purpose of calculating the weight percentage of the salt in the substantially pure salt, anything other than the salt, or a solvate or hydrate form thereof, is regarded as an impurity, which includes for example residual solvents, moisture contents, etc. For the avoidance of doubt, a composition comprising the substantially pure salt herein and one or more other ingredients should be understood as a mixture of the substantially pure salt herein and the one or more other ingredients, for example, such composition can be obtained directly or indirectly from mixing the substantially pure salt herein with the one or more other ingredients, such as water, pharmaceutically acceptable excipients, etc.

In some embodiments, the present invention provides a meglumine salt of Compound FA. Unless otherwise indicated to the contrary, the meglumine salt herein refers to a salt of Compound FA and meglumine in a 1:1 molar ratio. In any of the embodiments herein, the meglumine salt of Compound FA can be represented by the formula below:

The meglumine salt of Compound FA can exist in various crystalline forms. In some embodiments, the meglumine salt can exist in Form I. In some embodiments, the meglumine salt can exist in Form II. In some embodiments, the meglumine salt can exist in Form III, which is determined to be a dihydrate form. As used herein, when a salt is said to exist or be in one particular crystalline form, it should be understood that in some embodiments, the salt can exist substantially in that particular form. However, in some embodiments, the salt can also exist in the particular form, in a mixture with one or more other solid forms, including amorphous form. For example, in some embodiments, the meglumine salt can exist substantially in Form I, such as more than 80% by weight, more than 90% by weight, or more than 95% by weight, and in some embodiments, no other solid form can be identified, for example, by XRPD. In some embodiments, the meglumine salt can exist in Form I, in a mixture with one or more solid forms selected from Form II, III, and amorphous form.

Some embodiments of the present disclosure are directed to Form I of the meglumine salt of Compound FA. As detailed in the Examples section, although Compound FA can exist in a solid form, the solid form is characterized as having low crystallinity. Compared to Compound FA itself, Form I of the meglumine salt exhibited more desirable stability, solubility, and other physicochemical profile, some of which are exemplified in the Examples section. For example, Form I of the meglumine salt has higher aqueous solubility at both pH 1.2 and 6.8 compared to Compound FA. Further, Form I was found to have good storage stability. For example, Form I remained unchanged after storage under the condition of 25° C./92.5% RH for 10 days. Also, as shown in details in the Examples section, crystalline Form I was successfully scaled up and thus can be manufactured in large scale. See, e.g., Example 2. Thus, Form I of the meglumine salt can be more suited for various pharmaceutical applications.

Figure 1A:
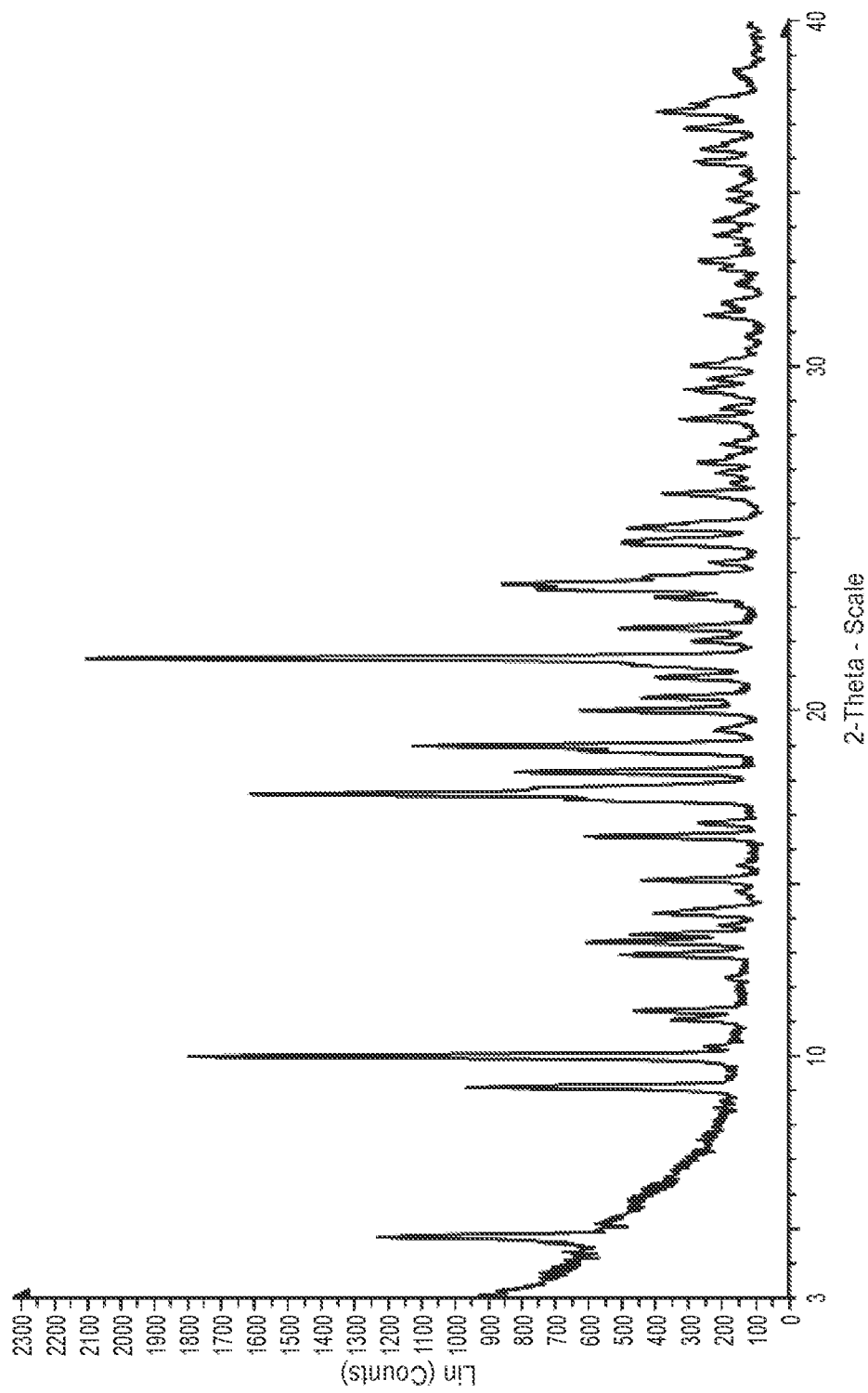
Figure 1B:
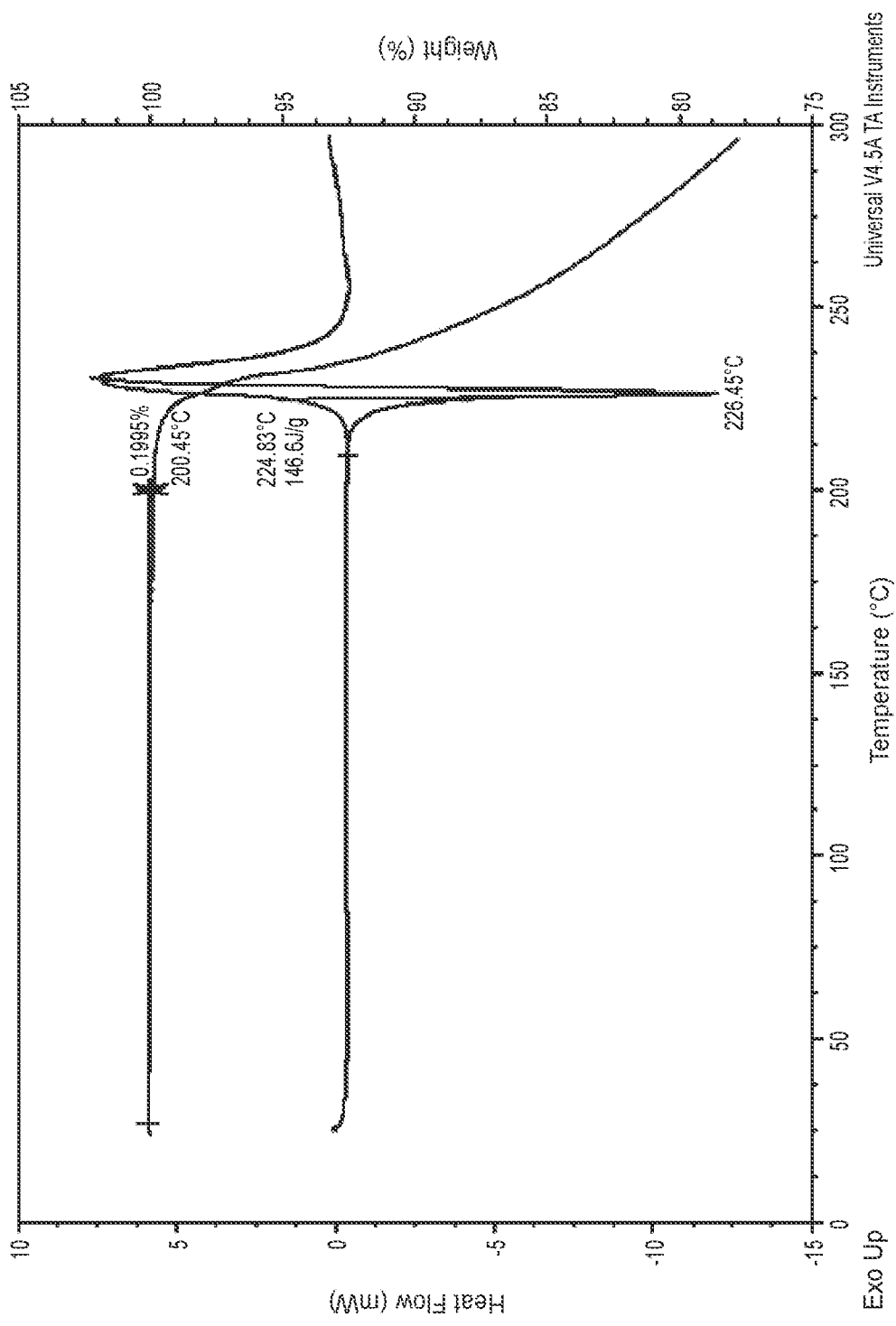

As used herein, Form I refers to a crystalline form of the meglumine salt of Compound FA, which can be characterized by (1) an XRPD pattern substantially the same as FIG. 1A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 1A, degrees 2 theta, ±0.2°; (3) an XRPD pattern having one or more (e.g., 1, 2, 3, 4, 5, 6, 7, or all) of the following peaks: 4.7, 9.1, 10.0, 17.6, 18.2, 19.0, 21.5, and 23.7 degrees 2 theta, ±0.2°; (4) an X-ray powder diffraction (XRPD) pattern having one or more (e.g., 8 or more, 12 or more, 16 or more, or 20 or more) of the following peaks: 4.7, 9.1, 10.0, 11.3, 13.0, 13.3, 13.5, 15.1, 16.4, 17.6, 18.2, 18.8, 19.0, 20.0, 20.4, 21.5, 22.4, 23.7, 23.9, 24.9, and 25.3 degrees 2 theta, ±0.2°; (5) a DSC pattern having an endotherm peak with an onset temperature of about 224.8° C. and/or peak temperature at about 226.5° C.; (6) a DSC profile substantially the same as shown in FIG. 1B; or any combination thereof (e.g., (1) and (5), (1) and (6), (2) and (5), (2) and (6), (3) and (5), (3) and (6), (4) and (5), or (4) and (6)). Major peaks of an XRPD spectrum as used herein refer to peaks having diffraction angles between 4-30 degrees (2 theta) and a relative intensity of 10% or above. In some embodiments, major peaks of an XRPD spectrum can refer to peaks with a relative intensity of 20% or above, 30% or above, 40% or above, 50% or above, 60% or above, 70% or above, 80% or above, or 90% or above. In some embodiments, the crystalline Form I can be characterized by an XRPD pattern having four or more (e.g., 4, 5, 6, 7, or all) of the following peaks: 4.7, 9.1, 10.0, 17.6, 18.2, 19.0, 21.5, and 23.7 degrees 2 theta, ±0.2°. In some embodiments, the crystalline Form I can be characterized by an XRPD pattern having all of the following peaks: 4.7, 9.1, 10.0, 17.6, 18.2, 19.0, 21.5, and 23.7 degrees 2 theta, ±0.2°.

Exemplary methods for preparing crystalline Form I of the meglumine salt are described herein. Typically, the method can include dissolving Compound FA in a solvent (e.g., methanol or isopropanol) to form a solution; adding about 1 equivalent of meglumine (e.g., in a methanol solution) to the solution to form the meglumine salt, which can be precipitated out. In some embodiments, Compound FA can also be suspended or partially dissolved in a solvent (e.g., methanol or isopropanol) to form a suspension or partial solution; and the method can include adding about 1 equivalent of meglumine (e.g., in a methanol solution) to the suspension or partial solution to form the meglumine salt, which can be precipitated out. Example of preparations of Form I are provided herein. In some embodiments, Form I can also be prepared from other crystalline forms of meglumine salts. As shown in Example 6D, when stirred at room temperature in isopropanol, the mixture of solids with Form I, II, and dihydrate (Form III) can be converted into crystalline Form I as a final predominant solid form. Similarly, a mixture of Form I and dihydrate form III, when heated at 60° C. in water, can also be converted into Form I as a final predominant solid form.

In some embodiments, Form I can be recrystallized under suitable conditions with various solvents or combinations. Suitable solvents for recrystallization include, but are not limited to, THF, toluene, MeOH, ethanol, n-propanol, isopropanol, isobutanol, methyl tert-butyl ether, ether, isoamylol, butyl acetate, ethyl formate, 1,4-dioxane, n-butanol, tert-butanol, n-heptane, cyclohexane, methyl isobutyl ketone, dimethylbenzene, isobutyl acetate, 2-butanone, acetonitrile, acetone, ethyl acetate, isopropyl acetate, and water. The solvents can be used alone or in various combinations. Recrystallization technics are generally known in the art. For example, the meglumine salt of Compound FA can be slurried in one or more of the solvents at room temperature or under heat; the meglumine salt of Compound FA can be heated in one or more of the solvents followed by cooling; the meglumine salt of Compound FA can be dissolved in a solvent and then an antisolvent is added; and other techniques such as solid/liquid diffusion or liquid/liquid diffusion can also be used.

Figure 2A:
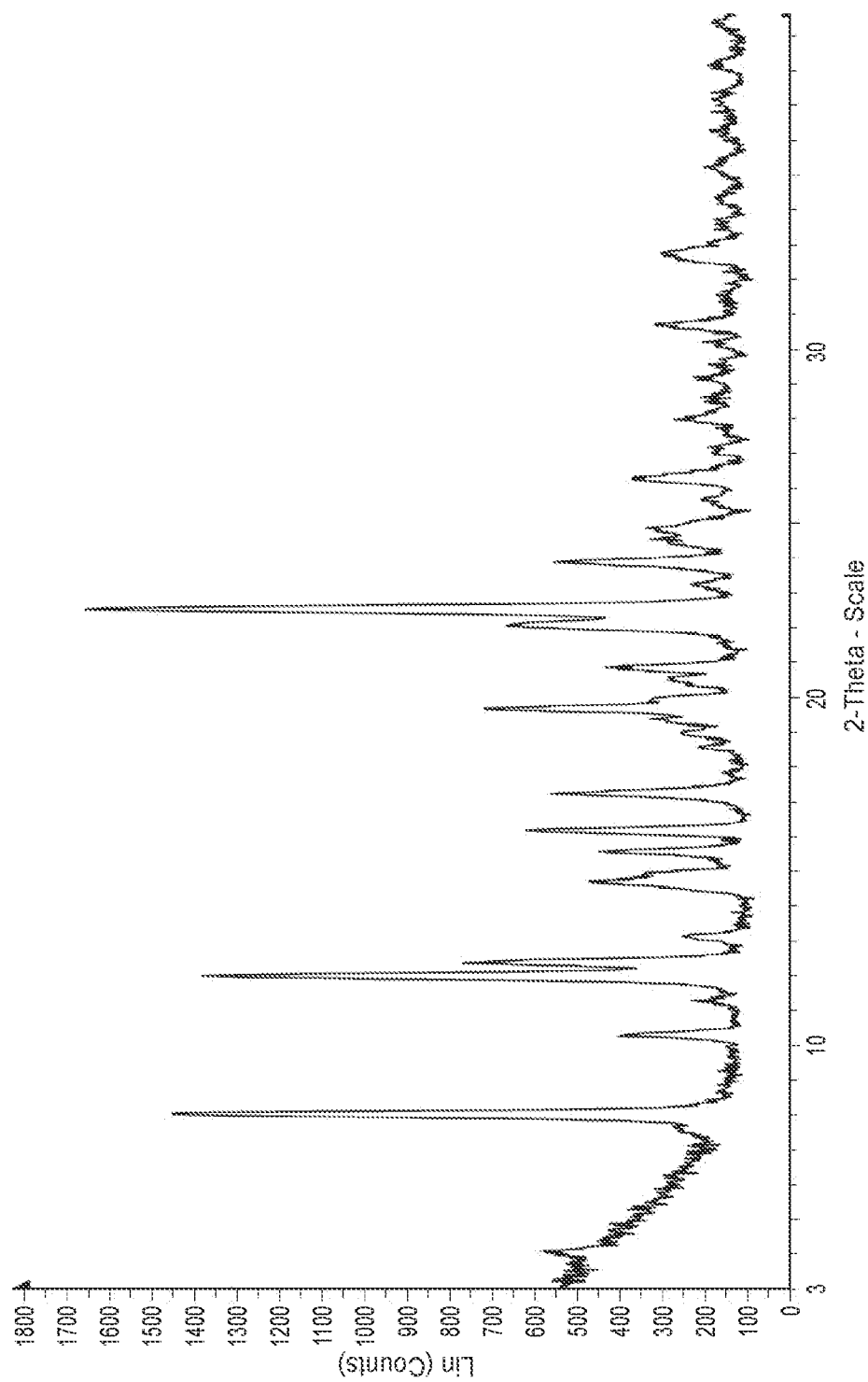
FIG. 2A shows a representative XRPD spectrum of crystalline form II of the meglumine salt of Compound FA.
Figure 2B:
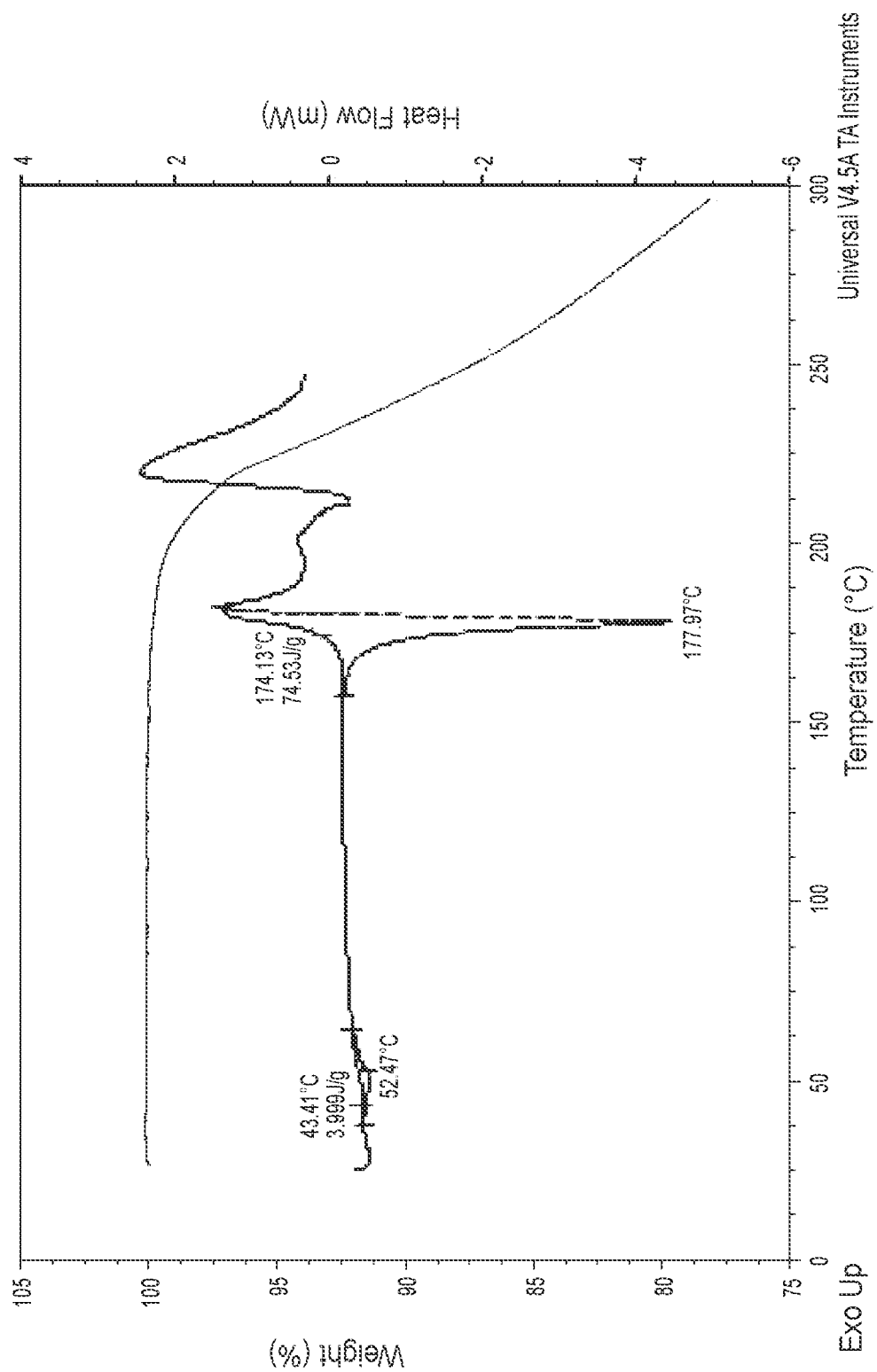
FIG. 2B shows a representative TGA and DSC analysis of crystalline form II of the meglumine salt of Compound FA.

Some embodiments of the present disclosure are directed to Form II of the meglumine salt of Compound FA. Form II can be prepared, for example, by drying the dihydrate form (Form III) of the meglumine salt of Compound FA. As used herein, Form II refers to a crystalline form of the meglumine salt of Compound FA, which can be characterized by (1) an XRPD pattern substantially the same as FIG. 2A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 2A, degrees 2 theta, ±0.2°; (3) an X-ray powder diffraction (XRPD) pattern having one or more (e.g., 1, 2, 3, 4, 5, 6, 7, 8, or 9) of the following peaks: 8.0, 12.0, 12.4, 16.1, 17.2, 19.7, 22.1, 22.5, and 23.9 degrees 2 theta, ±0.2°; (4) an X-ray powder diffraction (XRPD) pattern having one or more (e.g., 8 or more, 12 or more, or 16 or more) of the following peaks: 4.0, 8.0, 10.3, 12.0, 12.4, 14.7, 14.9, 15.5, 16.1, 17.2, 19.7, 20.8, 22.1, 22.5, 23.9, 24.5, 24.8, and 26.3 degrees 2 theta, ±0.2°; (5) a DSC pattern having an endotherm peak with an onset temperature of about 174.1° C. and/or a peak temperature at about 178.0° C.; (6) a DSC profile substantially the same as shown in FIG. 2B; or a combination thereof (e.g., (1) and (5), (1) and (6), (2) and (5), (2) and (6), (3) and (5), (3) and (6), (4) and (5), or (4) and (6)). For example, in some embodiments, the crystalline form II is characterized by an XRPD spectrum having four or more of the following peaks: 8.0, 12.0, 12.4, 16.1, 17.2, 19.7, 22.1, 22.5, and 23.9 degrees 2 theta, ±0.2°. In some embodiments, the crystalline form II is characterized by an XRPD spectrum having all of the following peaks: 8.0, 12.0, 12.4, 16.1, 17.2, 19.7, 22.1, 22.5, and 23.9 degrees 2 theta, ±0.2°.

Figure 3A:
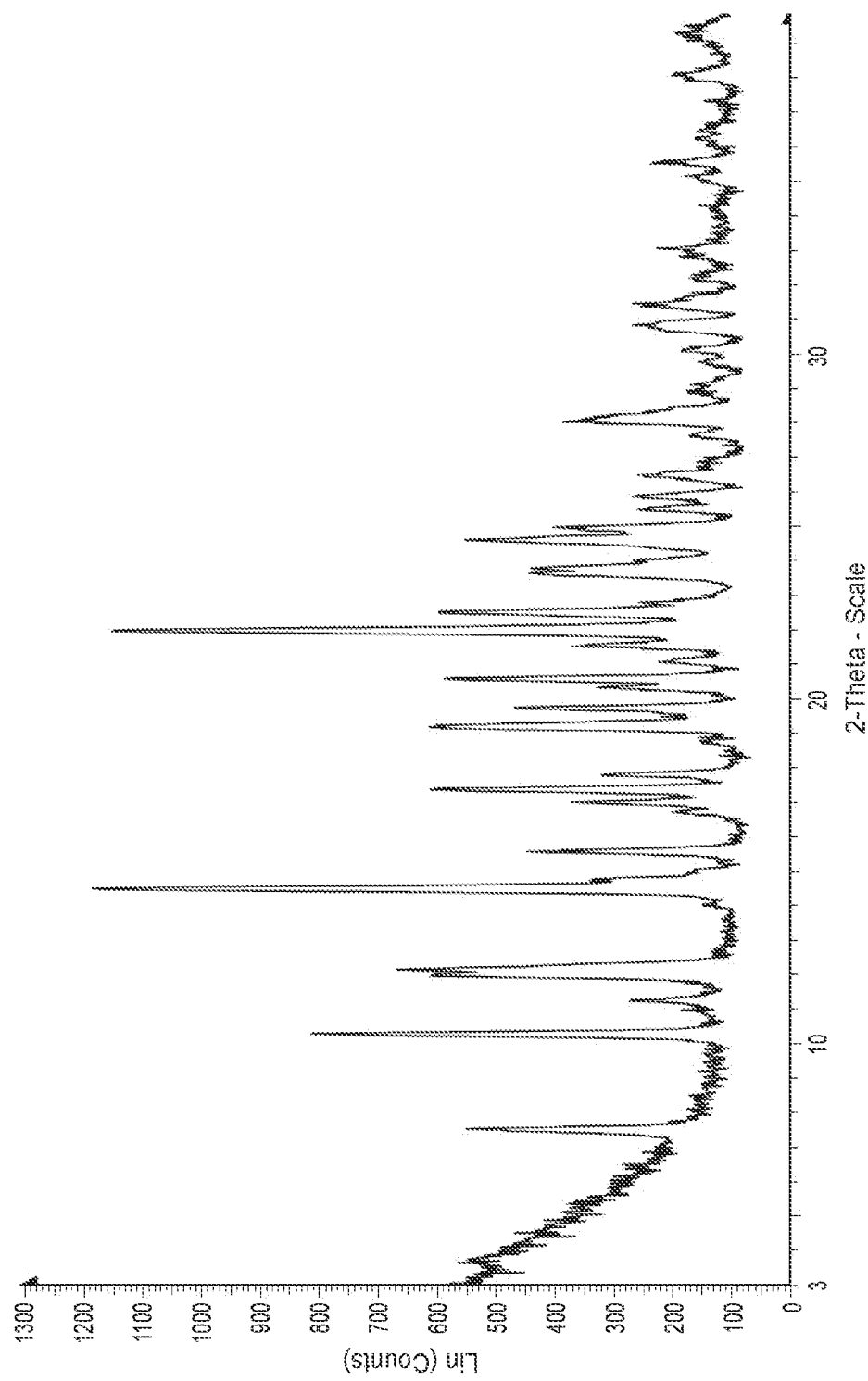
FIG. 3A shows a representative XRPD spectrum of crystalline form III (dihydrate) of the meglumine salt of Compound FA.
Figure 3B:
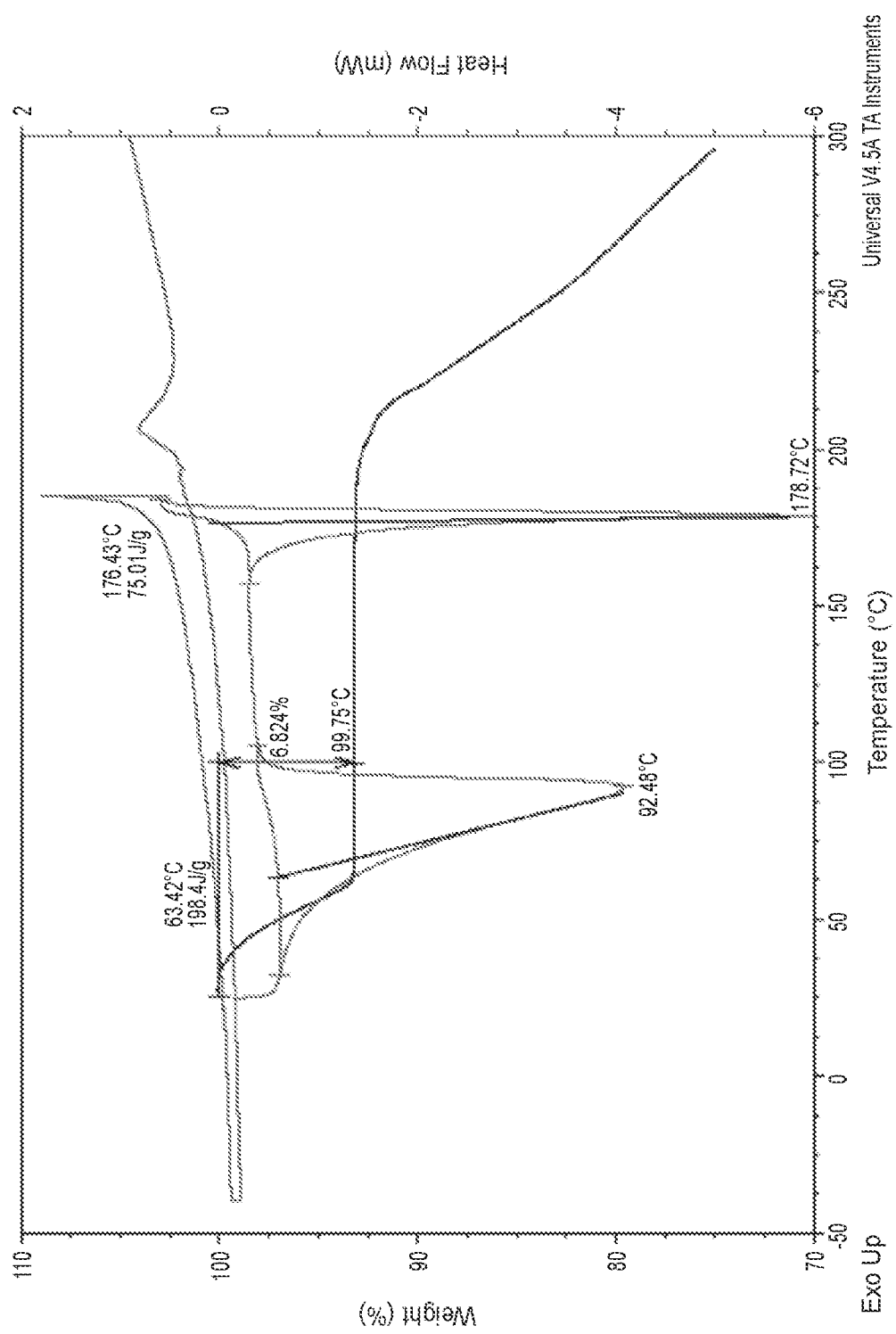
FIG. 3B shows a representative TGA and DSC analysis of crystalline form III of the meglumine salt of Compound FA.

The meglumine salt Form III is determined to be a hydrate form, more particularly, a dihydrate form. The dihydrate form III can be a stable solid form. For example, as shown in the interconversion experiment, stirring a mixture of Form I, II, and III in water at room temperature can result into the dihydrate form III as a final predominant solid form. Exemplary methods for preparing the dihydrate form are described in the Examples section. As used herein, Form III refers to a crystalline form of the meglumine salt of Compound FA, which can be characterized by (1) an XRPD pattern substantially the same as FIG. 3A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 3A, degrees 2 theta, ±0.2°; (3) an X-ray powder diffraction (XRPD) pattern having one or more (e.g., 1, 2, 3, 4, 5, 6, 7, 8, 9, 10, 11, 12, 13, 14, 15, 16, or 17) of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°; (4) an X-ray powder diffraction (XRPD) pattern having one or more (e.g., 8 or more, 12 or more, 16 or more, 20 or more, or 24 or more) of the following peaks: 3.7, 6.4, 7.5, 10.2, 11.2, 12.0, 14.5, 15.6, 17.0, 17.4, 17.8, 19.2, 19.7, 20.3, 20.6, 21.5, 22.0, 22.5, 22.8, 23.8, 24.6, 24.9, 25.5, 25.9, 26.5, 28.1, 30.9, and 31.4 degrees 2 theta, ±0.2°; (5) a DSC pattern having two endotherm peaks with onset temperatures of about 63.4° C. and 176.4° C. and/or respective peak temperatures at about 92.5° C. and 178.7° C.; (6) a DSC profile substantially the same as shown in FIG. 3B; or a combination thereof (e.g., (1) and (5), (1) and (6), (2) and (5), (2) and (6), (3) and (5), (3) and (6), (4) and (5), or (4) and (6)). For example, in some embodiments, the crystalline form III is characterized by an XRPD spectrum having four or more of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°. In some embodiments, the crystalline form III is characterized by an XRPD spectrum having eight or more of the following peaks: 7.5, 10.2, 12.0, 15.6, 17.0, 17.4, 19.2, 19.7, 20.6, 21.5, 22.0, 22.5, 23.8, 24.9, and 28.1 degrees 2 theta, ±0.2°. In some embodiments, the crystalline form III is characterized by an XRPD spectrum having twelve or more of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°. In some embodiments, the crystalline form III is characterized by an XRPD spectrum having all of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°.

In some embodiments, the present disclosure also provides a meglumine salt that can be produced by any of the following Procures 1-4.

Procedure 1: 23.45 mg of Compound FA was dissolved in 500 μL of 0.1 M meglumine/(methanol-water) solution. The clear solution was kept stirring for an hour. Concentrated and precipitation occurred. Add 200 μL of isopropyl acetate, and the solution became clear. Stirred for about 10 min, solid appeared. Added another 6004, of isopropyl acetate, and kept stirring for 20 min. The solid sample was collected by filtration. The sample was dry under vacuum overnight at 40° C.

Procedure 2: 24.02 mg of Compound FA was dissolved in 1 mL of 0.05 M meglumine/water solution. The clear solution was kept stirring at room temperature for an hour. Concentrated to about 50 μL, add 400 μL of isopropyl acetate. Stirred for about 10 min, solid appeared. Added another 200 μL of isopropyl acetate, and kept stirring for an hour. The solid sample was collected by filtration.

Procedure 3: 24.01 mg of Compound FA was dissolved in 500 μL of 0.1 M meglumine/(methanol-water) solution. The clear solution was kept stirring at room temperature for an hour. Concentrated to solid sample appeared, and added 400 μL of water. Stirred for 30 min, the product was obtained by filtration. Dry under vacuum overnight at 40° C., the sample was characterized.

Procedure 4: 23.13 mg of Compound FA was dissolved in 500 μL of IPA (isopropanol) with stirring at room temperature. Added 1 mL of 0.05 M meglumine/methanol solution. The clear solution was kept stirring at room temperature for an hour. Concentrated to solid sample appeared, and added 200 μL of IPA. Stirred for 30 min at room temperature, the product was obtained by filtration.

Figure 4A:
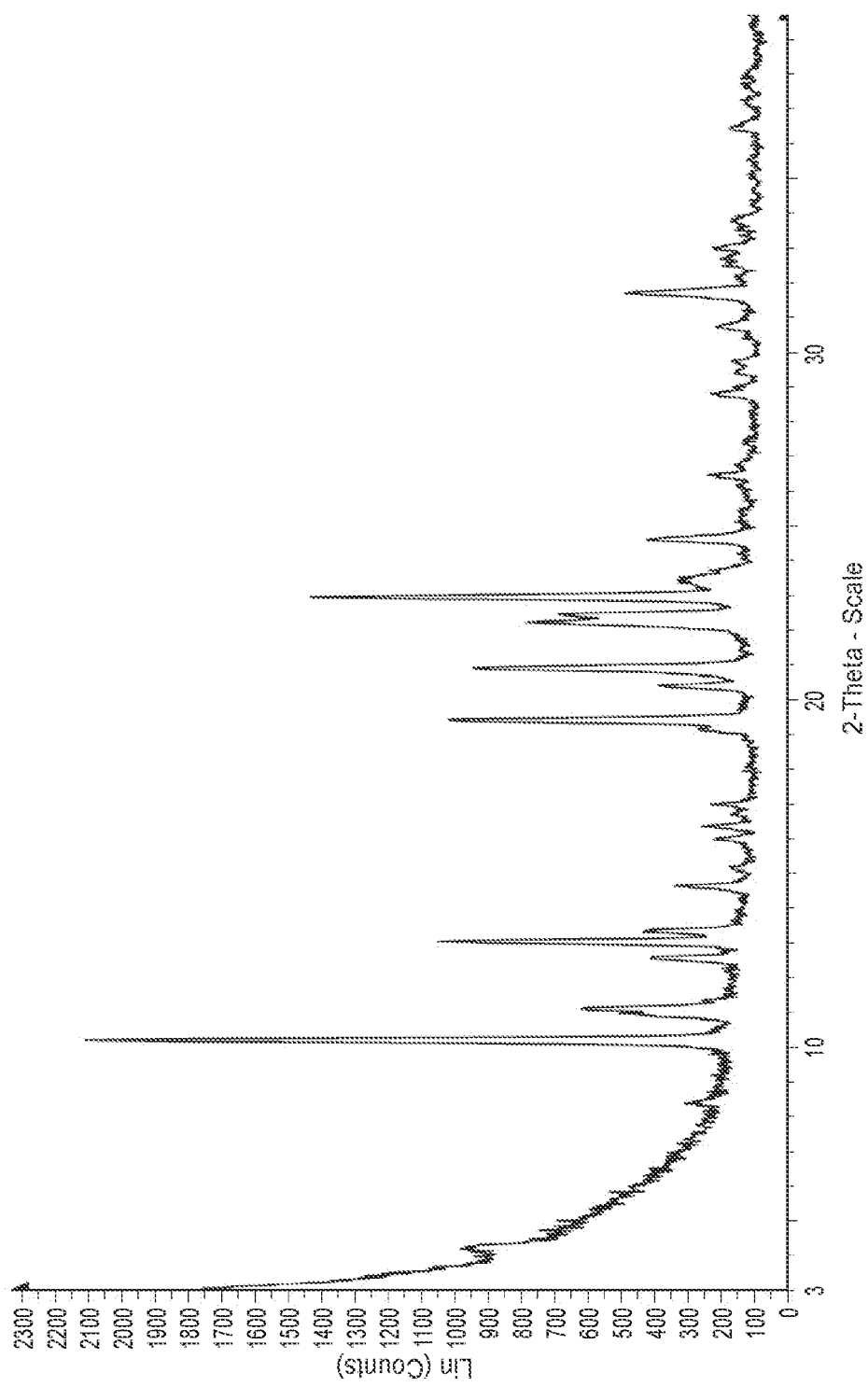
FIG. 4A shows a representative XRPD spectrum of crystalline form A of the L-lysine salt of Compound FA (1:1 molar ratio).
Figure 4B:
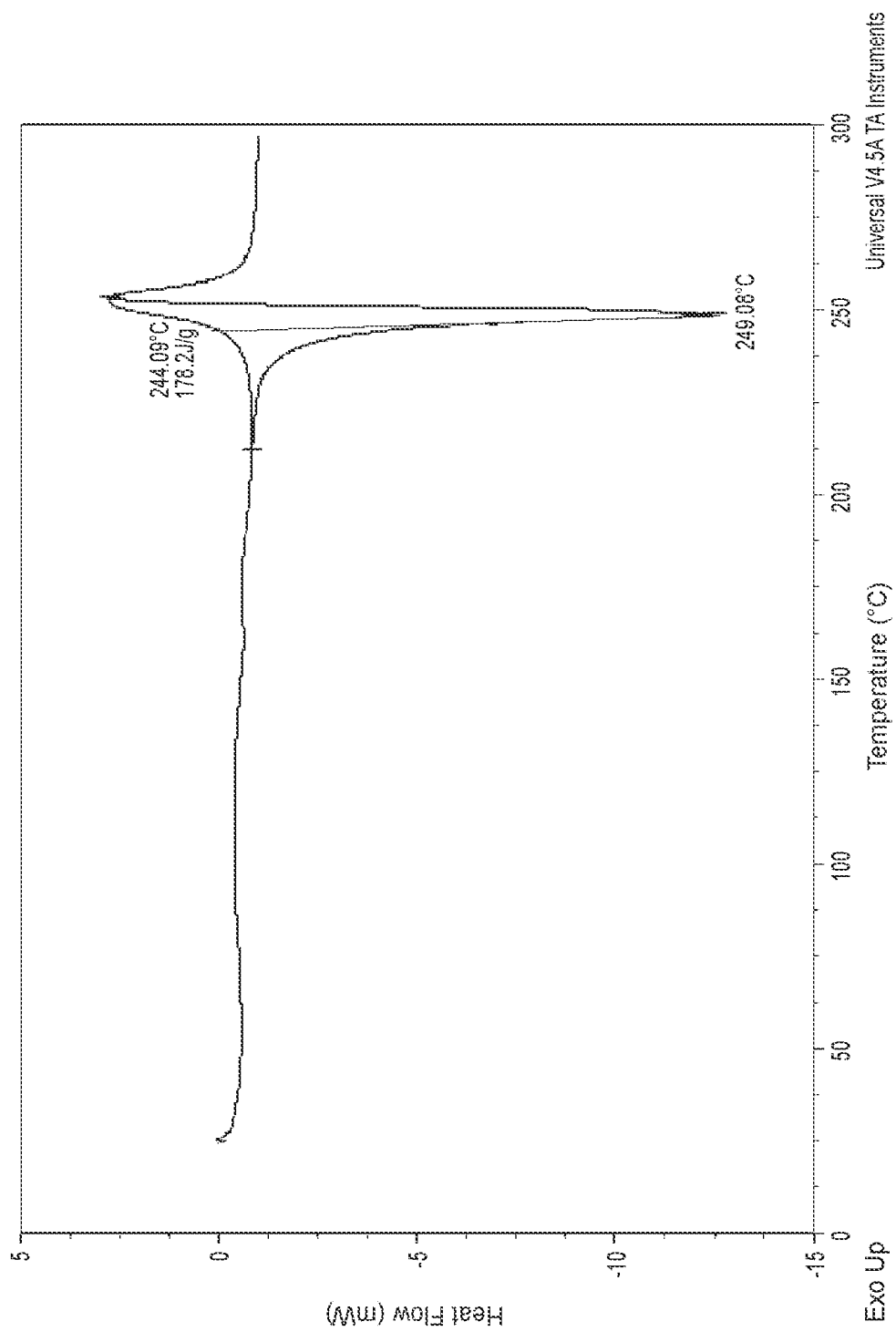
FIG. 4B shows a representative DSC analysis of the crystalline form A.

In some embodiments, the present disclosure also provides a lysine salt of Compound FA. In some embodiments, the lysine salt is an L-lysine salt with the molar ratio of lysine to Compound FA at about 1:1. In some embodiments, the L-lysine salt of Compound FA is in a crystalline form or an amorphous form, or a mixture thereof. In some embodiments, the L-lysine salt is in a crystalline Form A. Crystalline Form A as used herein refers to a crystalline form of the L-lysine salt of Compound FA (1:1 molar ratio), which can be characterized by (1) an XRPD pattern substantially the same as FIG. 4A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 4A, degrees 2 theta, ±0.2°; (3) an X-ray powder diffraction (XRPD) pattern having one or more (e.g., 1, 2, 3, 4, 5, 6, or 7) of the following peaks: 10.2, 13.0, 19.4, 20.9, 22.2, 22.4, and 22.9 degrees 2 theta, ±0.2°; (4) an X-ray powder diffraction (XRPD) pattern having one or more (e.g., 4 or more, 8 or more, 10 or more, or all) of the following peaks: 4.2, 10.2, 11.1, 13.0, 13.3, 19.4, 20.9, 22.2, 22.4, 22.9, 24.6, and 31.7 degrees 2 theta, ±0.2°; (5) a DSC pattern having an endotherm peak with an onset temperature of about 244.1° C. and/or a peak temperature at about 249.1° C.; (6) a DSC profile substantially the same as shown in FIG. 4B; or a combination thereof (e.g., (1) and (5), (1) and (6), (2) and (5), (2) and (6), (3) and (5), (3) and (6), (4) and (5), or (4) and (6)). In some embodiments, the crystalline form A is characterized by an XRPD spectrum having four or more of the following peaks: 10.2, 13.0, 19.4, 20.9, 22.2, 22.4, and 22.9 degrees 2 theta, ±0.2°. In some embodiments, the crystalline form A is characterized by an XRPD spectrum having all the following peaks: 10.2, 13.0, 19.4, 20.9, 22.2, 22.4, and 22.9 degrees 2 theta, ±0.2°.

In some embodiments, the present disclosure also provides a lysine salt that can be produced by any of the following Procures A-C.

Procedure A: 23.93 mg of Compound FA was dissolved in 400 μL of isobutanol with stirring at 50° C. Added 25 μL 1 M of L-lysine/water solution (0.5 eq.) and reacted at 50° C. Precipitation occurred in about 5 minutes. Reacted for another 20 min, the reaction solution was cooled slowly to room temperature. The sample was collected by filtration.

Procedure B: 24.00 mg of Compound FA was dissolved in 400 μL of isobutanol with stirring at 50° C. Added 50 μL 1 M of L-lysine/water solution (1 eq.) and reacted at 50° C. Precipitation occurred about 13 min later. Reacted for other 15 min, the reaction solution was cooled slowly to room temperature. The sample was collected by filtration.

Procedure C: 14.82 mg of lysine was added in 4784, of methanol. After stirring for 30 min at room temperature, solid sample could not dissolve. Added 43.88 mg of Compound FA, the solution was still cloudy. Kept stirring at room temperature overnight, the solid sample was obtained by filtration.

Some embodiments of the present disclosure are also directed to other amine salts. For example, in some embodiments, a trialkylamine salt of Compound FA is provided. Such trialkylamine salt can be used in a pharmaceutical composition directly or can be used to facilitate the manufacturing of Compound FA or its salts. See e.g., Example 2. In some embodiments, the trialkylamine salt is a diisopropylethyl amine salt. In some embodiments, the trialkyl amine salt is a diisopropylethyl amine salt of Compound FA represented by the structure below:

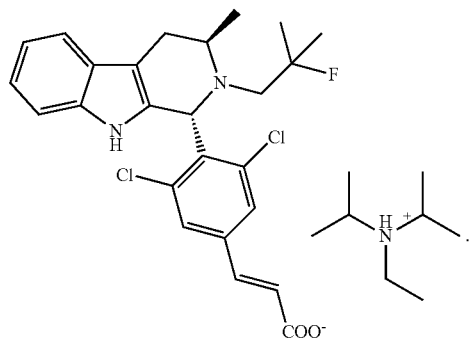

In some embodiments, the diisopropylethyl amine salt is in a crystalline form. In some embodiments, the diisopropylethyl amine salt can be in a solid form characterized by (1) an XRPD pattern substantially the same as shown in FIG. 8A; (2) an XRPD spectrum having the major peaks (e.g., peaks with relative intensity of 20% or above, 30% or above, 40% or above, 50% or above, 60% or above, 70% or above, 80% or above, or 90% or above) of FIG. 8A, degrees 2 theta, ±0.2°; (3) a DSC profile substantially the same as shown in FIG. 8B; or a combination thereof.

In some embodiments, the present disclosure also provides a tromethamine salt of Compound FA. In some embodiments, the tromethamine salt can be in a crystalline form or an amorphous form. In some embodiments, the tromethamine salt can be in a solid form characterized by (1) an XRPD pattern substantially the same as either of the two patterns in FIG. 5A; (2) an XRPD spectrum having the major peaks (e.g., peaks with relative intensity of 20% or above, 30% or above, 40% or above, 50% or above, 60% or above, 70% or above, 80% or above, or 90% or above) of either of the two patterns in FIG. 5A, degrees 2 theta, ±0.2°; (3) a DSC profile substantially the same as shown in FIG. 5B or 5C, respectively; or a combination thereof.

In some embodiments, the present disclosure also provides a choline salt of Compound FA. In some embodiments, the choline salt is in a crystalline form or an amorphous form. In some embodiments, the choline salt is a crystalline form that can be characterized by (1) an XRPD pattern substantially the same as the lower trace in FIG. 6A; (2) an XRPD spectrum having the major peaks (e.g., peaks with relative intensity of 20% or above, 30% or above, 40% or above, 50% or above, 60% or above, 70% or above, 80% or above, or 90% or above) of the lower trace in FIG. 6A, degrees 2 theta, ±0.2°; (3) a DSC profile substantially the same as shown in FIG. 6B, respectively; or a combination thereof. It should be noted that the top XRPD trace in FIG. 6A shows an amorphous form of the choline salt.

In some embodiments, the present disclosure also provides various other useful amine salts, such as arginine salt and ammonium salt.

Method of Synthesis

Some embodiments of the present disclosure are also directed to methods of preparing Compound FA or a salt (e.g., an amine salt) thereof. The process herein is advantageous in various aspects. For example, the method herein allows the formation of Compound FA from a tryptamine compound and an aldehyde without the need to protect the carboxylic acid function in the aldehyde compound.

In some embodiments, the method comprises reacting a tryptamine compound,

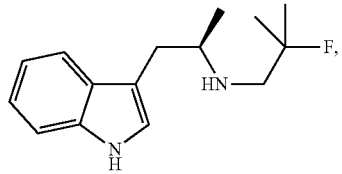 [SMILES: C[C@H](Cc1c[nH]c2ccccc12)NCC(C)(C)F]

or a salt thereof, with an aldehyde,

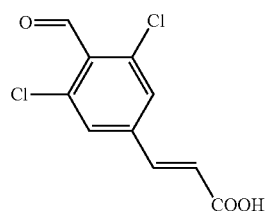 [SMILES: O=Cc1c(Cl)cc(/C=C/C(=O)O)cc1Cl]

or a salt thereof, under suitable conditions to form Compound FA

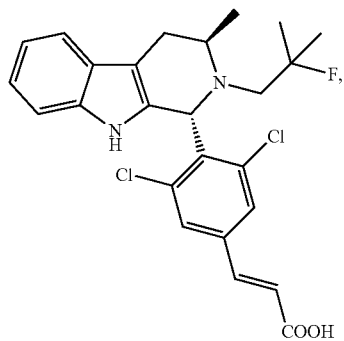 [SMILES: C[C@@H]1Cc2c([nH]c3ccccc23)[C@@H](c2c(Cl)cc(/C=C/C(=O)O)cc2Cl)N1CC(C)(C)F]

or a salt thereof. Various conditions are suitable for effecting the transformation, such as those known to be suitable for a Pictet-Spengler reaction. Some suitable conditions are also exemplified herein. In some embodiments, the reacting can take place in a solvent under heat, for example, in toluene under heat, such as at reflux temperature, to obtain Compound FA.

In some embodiments, an amine salt of Compound FA is desired. In such embodiments, the method further comprises converting Compound FA or a salt thereof into an amine salt of Compound FA. Typically, such conversion includes dissolving the Compound FA in a suitable solvent to form a compound FA solution and adding a suitable amount of amine (typically about 1:1 molar ratio) into the solution. After which, the amine salt can be obtained, for example, through recrystallization. In some embodiments, Compound FA can also be suspended or partially dissolved in a suitable solvent (e.g., methanol or isopropanol) to form a suspension or partial solution; and the method can include adding a suitable amount of amine (typically about 1:1 molar ratio) to the suspension or partial solution to form the amine salt.

For example, in some embodiments, a diisopropylethyl amine salt of Compound FA is desired. In some embodiments, the method can comprise reacting Compound FA or a salt thereof with diisopropylethyl amine to provide the diisopropylethyl amine salt of Compound FA:

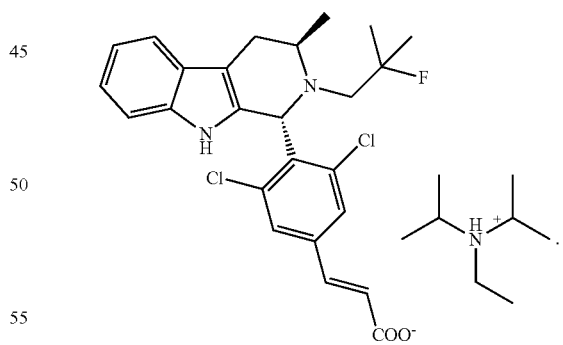

The diisopropylethyl amine salt can be in a crystalline form (e.g., described herein). In some embodiments, the diisoproylethyl amine salt can be used to facilitate manufacturing and/or purification of Compound FA or the meglumine salt of Compound FA. Examples of such usage are shown in Example 2.

In some embodiments, a meglumine amine salt of Compound FA is desired. In some embodiments, the method can comprise reacting Compound FA or a salt thereof with meglumine to provide the meglumine salt of Compound FA:

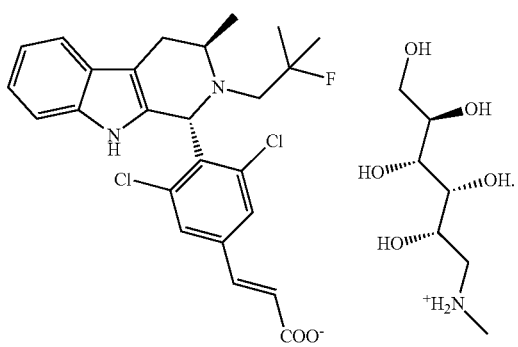
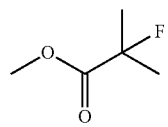

with a reducing agent (such as a boron reagent, such as NaBH$_4$) to form an alcohol

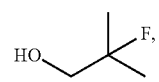

and subsequently reacting the alcohol with a triflate donor agent (such as triflate anhydride) to form

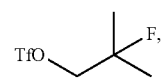

which is typically conducted in the presence of base, such as pyridine. Other conditions for reducing and converting into a triflate include those known in the art for such transformations. Alternatively, in some embodiments, the alcohol

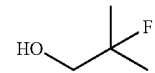

can be prepared by an epoxide ring opening of

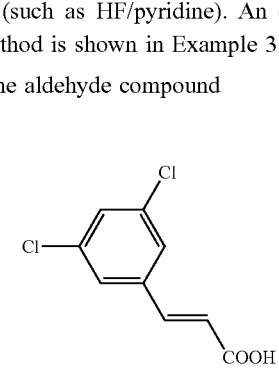

with fluoride (such as HF/pyridine). An example of this alternative method is shown in Example 3 herein.

Similarly, the aldehyde compound

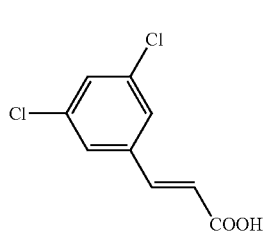

can be prepared by various methods. For example, in some embodiments, the aldehyde compound can be prepared by a process comprising converting a dichloro-compound, In some embodiments, the method can comprise reacting a diisopropylethyl amine salt of Compound FA with meglumine to provide the meglumine salt of Compound FA. In some embodiments, the diisopropylethyl amine salt can be first neutralized to form Compound FA, which is then followed by reacting with meglumine to form the meglumine salt. In some embodiments, the meglumine salt can be further recrystallized to form Form I, II, or III of the meglumine salt of Compound FA. In some embodiments, the meglumine salt can also be made into an amorphous form, or an amorphous form in a mixture with any of Form I, II, and/or III.

The tryptamine compound can be obtained by various methods, which are not limited to any particular routes of synthesis. In some embodiments, the tryptamine compound can be prepared by a process comprising reacting a fluorotriflate compound

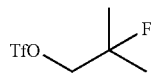

with

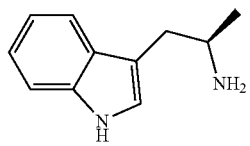

in the presence of a base, such as a trialkylamine, such as diisopropylethyl amine.

The fluorotriflate compound

can also be obtained by various methods, which are not limited to any particular route of synthesis. In some embodiments, the

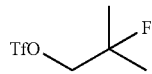

can be prepared by a process comprising reducing

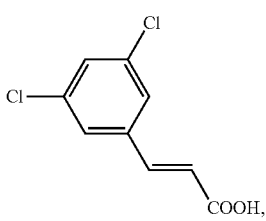 [SMILES: O=C(O)/C=C/c1cc(Cl)cc(Cl)c1]

into an anionic intermediate with a base, which is subsequently reacted with an aldehyde donor agent to form

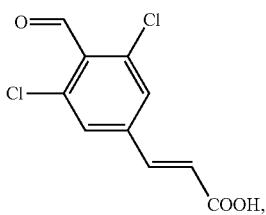 [SMILES: O=Cc1c(Cl)cc(/C=C/C(=O)O)cc1Cl]

or a salt thereof. Typically, the base used is a strong base such as lithium diisopropylamide. Aldehyde donor agents are known in the art, which include any compound that can react with the anionic intermediate to form a benzaldehyde, for example, dimethylformamide can be used as an aldehyde donor agent herein.

In some embodiments, the method is substantially the same as those described in Example 2.

In some embodiments, the present disclosure is also directed to any products produced by any of the methods herein, and methods of using such products.

Pharmaceutical Compositions

In various embodiments, the present disclosure also provides pharmaceutical compositions comprising a salt of the present disclosure, such as an amine salt described herein, and optionally a pharmaceutically acceptable excipient. In certain embodiments, a pharmaceutical composition described herein comprises a salt of the present disclosure, such as an amine salt described herein, and a pharmaceutically acceptable excipient. The pharmaceutical compositions described herein are useful in treating and/or preventing proliferative diseases (e.g., ER+ breast cancer) or diseases associated with ER.

In some embodiments, the present invention provides a pharmaceutical composition comprising one or more of the salts of the present disclosure (e.g., the amine salts of Compound FA, such as Form I, II, or III of meglumine salt of Compound FA or Form A of the lysine salt of Compound FA). Typically, the pharmaceutical composition comprises a therapeutically effective amount of one or more of the salts of the present disclosure (e.g., Form I, II, or III of meglumine salt of Compound FA or Form A of the lysine salt of Compound FA) and optionally a pharmaceutically acceptable excipient or carrier. In some embodiments, the pharmaceutical composition comprises one or more of the substantially pure amine salts as described herein. In some embodiments, the pharmaceutical composition comprises one or more of the crystalline forms selected from Form I, II, III of meglumine salt of Compound FA and Form A of the lysine salt of Compound FA.

In some specific embodiments, the pharmaceutical composition comprises Form I of the meglumine salt of Compound FA. In some specific embodiments, the active ingredient in the pharmaceutical composition can comprise, consist essentially of, or consist of the meglumine salt of Compound FA in Form I. In some embodiments, Compound FA exists in the pharmaceutical composition essentially in Form I, for example, at least 80% (e.g., at least 85%, at least 90%, at least 95%, by weight of total Compound FA) of Compound FA exist in the pharmaceutical composition in Form I. In some embodiments, the pharmaceutical composition is substantially free of Compound FA in any other solid form, such as other salts or other crystalline forms. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than meglumine salt of Compound FA (1:1 molar ratio). In some embodiments, the pharmaceutical composition is free or substantially free of Compound FA in a crystalline form other than Form I of the meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form I. Weight of total Compound FA in a pharmaceutical composition, as used herein, refers to the weight of all forms of Compound FA combined, including for example, free acid form, salts, crystalline forms, amorphous forms, hydrates, solvates etc., expressed in equivalent weight of Compound FA as a free acid. For the calculation of the weight percentages of each different form in a given pharmaceutical composition, it should be clear to those skilled in the art that the weight of each different form will be first converted into its respective equivalent weight of Compound FA as a free acid, which is then divided by the weight of total Compound FA as defined herein.

In some specific embodiments, the active ingredient in the pharmaceutical composition can comprise, consist essentially of, or consist of the meglumine salt of Compound FA in Form I, amorphous form, or a mixture thereof. In some embodiments, Compound FA can exist in the pharmaceutical composition as a mixture of Form I and an amorphous form of the meglumine salt of Compound FA, for example, at least 80% (e.g., at least 85%, at least 90%, at least 95%, by weight of total Compound FA) of Compound FA can exist in the pharmaceutical composition in Form I or an amorphous form.

In some specific embodiments, the pharmaceutical composition comprises Form II of the meglumine salt of Compound FA. In some specific embodiments, the active ingredient in the pharmaceutical composition can comprise, consist essentially of, or consist of the meglumine salt of Compound FA in Form II. In some embodiments, Compound FA exists in the pharmaceutical composition essentially in Form II, for example, at least 80% (e.g., at least 85%, at least 90%, at least 95%, by weight of total Compound FA) of Compound FA exist in the pharmaceutical composition in Form II. In some embodiments, the pharmaceutical composition is substantially free of Compound FA in any other solid forms, such as other salts or other crystalline form. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than meglumine salt of Compound FA (1:1 molar ratio). In some embodiments, the pharmaceutical composition is free or substantially free of Compound FA in a crystalline form other than Form II of the meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form II. In some specific embodiments, the active ingredient in the pharmaceutical composition can comprise, consist essentially of, or consist of the meglumine salt of Compound FA in Form II, amorphous form, or a mixture thereof. In some embodiments, Compound FA can exist in the pharmaceutical composition as a mixture of Form II and an amorphous form of the meglumine salt of Compound FA, for example, at least 80% (e.g., at least 85%, at least 90%, at least 95%, by weight of total Compound FA) of Compound FA can exist in the pharmaceutical composition in Form II or an amorphous form.

In some specific embodiments, the pharmaceutical composition comprises Form III of the meglumine salt of Compound FA. In some specific embodiments, the active ingredient in the pharmaceutical composition can comprise, consist essentially of, or consist of the meglumine salt of Compound FA in Form III. In some embodiments, Compound FA exists in the pharmaceutical composition essentially in Form III, for example, at least 80% (e.g., at least 85%, at least 90%, at least 95%, by weight of total Compound FA) of Compound FA exist in the pharmaceutical composition in Form III. In some embodiments, the pharmaceutical composition is substantially free of Compound FA in any other solid forms, such as other salts or other crystalline form. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than meglumine salt of Compound FA (1:1 molar ratio). In some embodiments, the pharmaceutical composition is free or substantially free of Compound FA in a crystalline form other than Form III of the meglumine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form III. In some specific embodiments, the active ingredient in the pharmaceutical composition can comprise, consist essentially of, or consist of the meglumine salt of Compound FA in Form III, amorphous form, or a mixture thereof. In some embodiments, Compound FA can exist in the pharmaceutical composition as a mixture of Form III and an amorphous form of the meglumine salt of Compound FA, for example, at least 80% (e.g., at least 85%, at least 90%, at least 95%, by weight of total Compound FA) of Compound FA can exist in the pharmaceutical composition in Form III or an amorphous form.

Typically, the pharmaceutical composition comprising the meglumine salt of Compound FA (e.g., in Form I, II, III, and/or amorphous form) does not include a significant amount of Compound FA as a free acid. In some embodiments, the pharmaceutical composition described herein above can also include a mixture of the meglumine salt and the free acid form (other than and in addition to any amount that may exist through equilibrium).

Other salts, for example, any one or more of other amine salts of Compound FA described herein, such as the L-lysine salt of Compound FA (1:1 molar ratio), can be formulated similarly to those described herein for the meglumine salt of Compound FA, such as Form I.

For example, in some embodiments, the pharmaceutical composition can comprise Form A of the L-lysine salt of Compound FA. In some specific embodiments, the active ingredient in the pharmaceutical composition can comprise, consist essentially of, or consist of the L-lysine salt of Compound FA in Form A. In some embodiments, Compound FA exists in the pharmaceutical composition essentially in Form A, for example, at least 80% (e.g., at least 85%, at least 90%, at least 95%, by weight of total Compound FA) of Compound FA exist in the pharmaceutical composition in Form A. In some embodiments, the pharmaceutical composition is substantially free of Compound FA in any other solid form, such as other salts or other crystalline form. For example, in some embodiments, the pharmaceutical composition is free or substantially free of Compound FA in its free acid form, for example, the pharmaceutical composition can in some embodiments include less than 10%, less than 5%, less than 2%, less than 1%, by weight of total Compound FA, or non-detectable amount, of Compound FA in its free acid form. In some embodiments, the pharmaceutical composition is free or substantially free of Compound FA in a salt form other than L-lysine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a salt form other than L-lysine salt of Compound FA (1:1 molar ratio). In some embodiments, the pharmaceutical composition is free or substantially free of Compound FA in a crystalline form other than Form A of the L-lysine salt of Compound FA (1:1 molar ratio), for example, the pharmaceutical composition can in some embodiments include less than 10%, less than 5%, less than 2%, less than 1%, by weight of total Compound FA, or non-detectable amount, of Compound FA in a crystalline form other than Form A. However, in some embodiments, the pharmaceutical composition can also comprise amorphous form of the L-lysine salt of FA (1:1 molar ratio).

Others salts such as the tromethamine salts, choline salts, etc. can be formulated similarly.

Typically, the salt of the present disclosure (e.g., the amine salts of Compound FA, such as Form I, II, or III of meglumine salt of Compound FA or Form A of the lysine salt of Compound FA) is provided in an effective amount in the pharmaceutical composition. In certain embodiments, the effective amount is a therapeutically effective amount (e.g., amount effective for treating a proliferative disease in a subject in need thereof). In certain embodiments, the proliferative disease is cancer, e.g., ER+ breast cancer. In certain embodiments, the effective amount is a prophylactically effective amount (e.g., amount effective for preventing a proliferative disease in a subject in need thereof and/or for keeping a subject in need thereof in remission of a proliferative disease).

Pharmaceutical compositions described herein can be prepared by any method known in the art of pharmacology. In general, such preparatory methods include bringing the active ingredient, such as the salt of the present disclosure, into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients useful for the manufacture of the pharmaceutical compositions herein include, for example, inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The pharmaceutical composition can be formulated for any routes of administration, for example, oral administration. Typically, the pharmaceutical composition is a solid dosage form. However, in some embodiments, other dosage forms such as liquid, suspension, or semi-solid dosage forms can also be used.

Solid dosage forms for oral administration include for example capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient (e.g., the salts of the present disclosure) can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The salts of the present disclosure are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or salt described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition herein or salt of the present disclosure. In some embodiments, the pharmaceutical composition or salt of the present disclosure provided in the first container and the second container are combined to form one unit dosage form.

In certain embodiments, a kit described herein includes a first container comprising a salt of the present disclosure or pharmaceutical composition described herein. In certain embodiments, a kit described herein is useful in treating a proliferative disease (e.g., ER+ breast cancer) in a subject in need thereof, and/or preventing a proliferative disease in a subject in need thereof. In some embodiments, the SERDs described herein are useful in treating diseases and/or disorders associated with a steroid hormone such as estrogen.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, and/or preventing a proliferative disease in a subject in need thereof. A kit described herein may include one or more additional pharmaceutical agents described herein as a separate composition. In some embodiments, the one or more additional agents can be one or more additional antiproliferative agents, which can be included with the salt herein in the same or a separate composition. In some embodiments, the antiproliferative agent can be a CDK4/CDK6 inhibitor, such as pabociclib.

Methods of Treatment

The salts of the present disclosure and pharmaceutical compositions described herein are useful in treating and/or preventing proliferative diseases and/or a disease associated with a steroid hormone such as estrogen. As discussed in WO2017/136688, the content of which is hereby incorporated by reference in its entirety, SERDs such as Compound FA induced degradation of ER and inhibited the growth of ER+ breast cancer cells and exhibited better human hepatocyte clearance than drug of the same class such as fulvestrant, as well as those in clinical trials such as GDC-0810 and AZD9496.

Accordingly, in some embodiments, the present disclosure also provides methods of treating a proliferative disease and/or a disease associated with a steroid hormone such as estrogen, in a subject in need thereof, the methods comprising administering to the subject an effective amount (e.g., therapeutically effective amount) of a salt of the present disclosure (e.g., the amine salts of Compound FA, such as Form I, II, or III of meglumine salt of Compound FA or Form A of the lysine salt of Compound FA), or pharmaceutical composition described herein.

In some embodiments, the present disclosure also provide a method of preventing a proliferative disease and/or a disease associated with a steroid hormone such as estrogen, in a subject in need thereof, the methods comprising administering to the subject an effective amount (e.g., prophylactically effective amount) of a salt of the present disclosure (e.g., the amine salts of Compound FA, such as Form I, II, or III of meglumine salt of Compound FA or Form A of the lysine salt of Compound FA), or a pharmaceutical composition described herein.

In certain embodiments, the method is for treating and/or preventing cancer. In certain embodiments, the cancer is breast cancer. In certain embodiments, the method is for treating and/or preventing gynecological disease or cancer associated with ER such as cancer of the ovary, cervix or endometrium and breast cancer, particularly ER+ breast cancer. In some embodiments, the cancer (e.g., breast cancer, such as ER+ breast cancer) is resistant to estrogen modulators such as tamoxifen and/or aromatase inhibitors.

In certain embodiments, the method described herein further includes administering to the subject an additional pharmaceutical agent such as an additional antiproliferative agent. In some embodiments, the antiproliferative agent can be a CDK4/CDK6 inhibitor, such as pabociclib. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the method described herein further includes radiotherapy, immunotherapy, and/or transplantation (e.g., bone marrow transplantation).

The salts and/or compositions of the present disclosure can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The salts and/or compositions of the present disclosure can be administered in combination with one or more additional pharmaceutical agents (e.g., therapeutically and/or prophylactically active agents) useful in treating and/or preventing a proliferative disease. The salts or compositions can be administered in combination with additional pharmaceutical agents that improve their activity (e.g., activity (e.g., potency and/or efficacy) in treating a proliferative disease in a subject in need thereof, and/or in preventing a proliferative disease in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a salt of the present disclosure and an additional pharmaceutical agent shows a synergistic effect that is absent in a pharmaceutical composition including one of the compound and the additional pharmaceutical agent, but not both.

The salt or composition of the present disclosure can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agents may also be administered together with each other and/or with the salt or composition of the present disclosure in a single dose or administered separately in different doses. The particular combination to employ in a regimen will take into account compatibility of the salt of the present disclosure with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent, for example, an immune-oncology agents (e.g., anti-PD-1 antibody) or cells (e.g., CAR-T cells)). In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the salts of the present disclosure or pharmaceutical compositions can be administered in combination with an anti-cancer therapy including, but not limited to, targeted therapy (e.g., mTOR signaling pathway inhibitor), cell therapy, surgery, radiation therapy, immunotherapy, and chemotherapy (e.g., docetaxel, doxorubicin).

ALTERNATIVE EMBODIMENTS

Embodiment 1. An amine salt (e.g., pharmaceutically acceptable amine salt) of (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid ("Compound FA"):

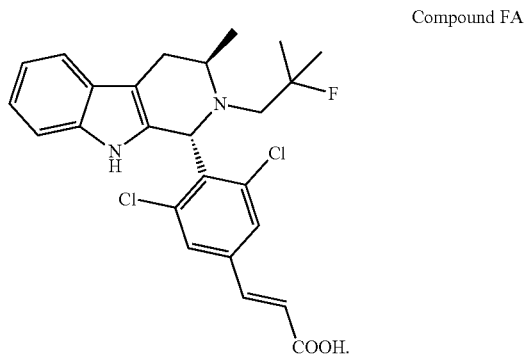 [SMILES: C[C@@H]1Cc2c([nH]c3ccccc23)[C@@H](c2c(Cl)cc(/C=C/C(=O)O)cc2Cl)N1CC(C)(C)F]

Compound FA

Embodiment 2. The amine salt of embodiment 1, which is a meglumine salt, trialkyl amine salt, lysine salt, arginine salt, tromethamine salt, choline salt, or ammonium salt, e.g., in a solid form such as in a crystalline form or an amorphous form, or a mixture thereof.

Embodiment 3. The amine salt of embodiment 2, which is a meglumine salt of Compound FA represented by the structure below:

Embodiment 4. The amine salt of embodiment 3, which is in Form I of the meglumine salt, which is characterized by (1) an X-ray powder diffraction (XRPD) pattern having one or more (e.g., 1, 2, 3, 4, 5, 6, 7, or 8) of the following peaks: 4.7, 9.1, 10.0, 17.6, 18.2, 19.0, 21.5, and 23.7 degrees 2 theta, ±0.2°; (2) an X-ray powder diffraction (XRPD) pattern having one or more (e.g., 8 or more, 12 or more, 16 or more, or 20 or more) of the following peaks: 4.7, 9.1, 10.0, 11.3, 13.0, 13.3, 13.5, 15.1, 16.4, 17.6, 18.2, 18.8, 19.0, 20.0, 20.4, 21.5, 22.4, 23.7, 23.9, 24.9, and 25.3 degrees 2 theta, ±0.2°; (3) an XRPD pattern substantially the same as shown in FIG. 1A; (4) a Differential Scanning calorimetry (DSC) pattern substantially the same as shown in FIG. 1B; or any combination thereof (e.g., (1) and (4), (2) and (4), or (3) and (4)).

Embodiment 5. The amine salt of embodiment 3 which is in Form II of the meglumine salt, which is characterized by (1) an X-ray powder diffraction (XRPD) pattern having one or more (e.g., 1, 2, 3, 4, 5, 6, 7, 8, or 9) of the following peaks: 8.0, 12.0, 12.4, 16.1, 17.2, 19.7, 22.1, 22.5, and 23.9 degrees 2 theta, ±0.2°; (2) an X-ray powder diffraction (XRPD) pattern having one or more (e.g., 8 or more, 12 or more, or 16 or more) of the following peaks: 4.0, 8.0, 10.3, 12.0, 12.4, 14.7, 14.9, 15.5, 16.1, 17.2, 19.7, 20.8, 22.1, 22.5, 23.9, 24.5, 24.8, and 26.3 degrees 2 theta, ±0.2°; (3) an XRPD pattern substantially the same as shown in FIG. 2A; (4) a Differential Scanning calorimetry (DSC) pattern substantially the same as shown in FIG. 2B; or any combination thereof (e.g., (1) and (4), (2) and (4), or (3) and (4)).

Embodiment 6. The amine salt of embodiment 3, which is in Form III of the meglumine salt, which is characterized by (1) an X-ray powder diffraction (XRPD) pattern having one or more (e.g., 1, 2, 3, 4, 5, 6, 7, 8, 9, 10, 11, 12, 13, 14, 15, 16, or 17) of the following peaks: 7.5, 10.2, 12.0, 14.5, 15.6, 17.0, 17.4, 19.2, 19.7, 20.6, 21.5, 22.0, 22.5, 23.8, 24.6, 24.9, and 28.1 degrees 2 theta, ±0.2°; (2) an X-ray powder diffraction (XRPD) pattern having one or more (e.g., 8 or more, 12 or more, 16 or more, 20 or more, or 24 or more) of the following peaks: 3.7, 6.4, 7.5, 10.2, 11.2, 12.0, 14.5, 15.6, 17.0, 17.4, 17.8, 19.2, 19.7, 20.3, 20.6, 21.5, 22.0, 22.5, 22.8, 23.8, 24.6, 24.9, 25.5, 25.9, 26.5, 28.1, 30.9, and 31.4 degrees 2 theta, ±0.2°; (3) an XRPD pattern substantially the same as shown in FIG. 3A; (4) a Differential Scanning calorimetry (DSC) pattern substantially the same as shown in FIG. 3B; or any combination thereof (e.g., (1) and (4), (2) and (4), or (3) and (4)).

Embodiment 7. The amine salt of embodiment 2, which is an L-lysine salt of Compound FA.

Embodiment 8. The amine salt of embodiment 7, which is in Form A of the L-lysine salt, which is characterized by (1) an X-ray powder diffraction (XRPD) pattern having one or more (e.g., 1, 2, 3, 4, 5, 6, or 7) of the following peaks: 10.2, 13.0, 19.4, 20.9, 22.2, 22.4, and 22.9 degrees 2 theta, ±0.2°; (2) an X-ray powder diffraction (XRPD) pattern having one or more (e.g., 4 or more, 8 or more, 10 or more, or all) of the following peaks: 4.2, 10.2, 11.1, 13.0, 13.3, 19.4, 20.9, 22.2, 22.4, 22.9, 24.6, and 31.7 degrees 2 theta, ±0.2°; (3) an XRPD pattern substantially the same as shown in FIG. 4A; (4) a Differential Scanning calorimetry (DSC) pattern substantially the same as shown in FIG. 4B; or any combination thereof (e.g., (1) and (4), (2) and (4), or (3) and (4)).

Embodiment 9. The amine salt of embodiment 2, which is a diisopropylethyl amine salt of Compound FA represented by the structure below:

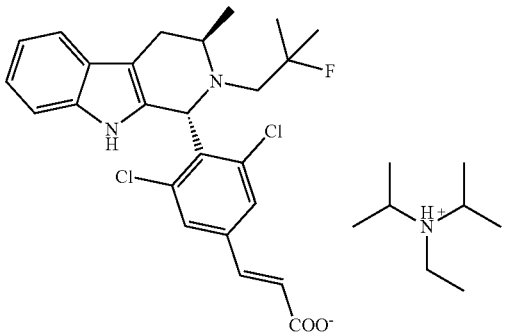

Embodiment 10. The amine salt of embodiment 9, which is in a crystalline form.

Embodiment 11. The amine salt of embodiment 2, which is a tromethamine salt of Compound FA.

Embodiment 12. The amine salt of embodiment 11, which is in a crystalline form.

Embodiment 13. The amine salt of embodiment 2, which is a choline salt of Compound FA.

Embodiment 14. The amine salt of embodiment 13, which is in a crystalline form.

Embodiment 15. The amine salt of embodiment 2, which is an ammonium salt or an arginine salt of Compound FA.

Embodiment 16. A pharmaceutical composition comprising an amine salt of any one of embodiments 1-15, and optionally a pharmaceutically acceptable excipient.

Embodiment 17. A method of treating a proliferative disease, the method comprising administering to a subject in need thereof an effective amount of an amine salt of any one of embodiments 1-15 or a pharmaceutical composition of embodiment 16.

Embodiment 18. The method of embodiment 17, wherein the proliferative disease is cancer.

Embodiment 19. The method of embodiment 17, wherein the cancer is breast cancer or a gynecological disease or cancer.

Embodiment 20. The method of embodiment 18 or 19, wherein the cancer is ER+ breast cancer or gynecological disease or cancer associated with ER.

Embodiment 21. The method of any one of embodiments 17-20, further comprising administering to the subject an effective amount of an additional antiproliferative agent.

Embodiment 22. The method of embodiment 21, wherein the additional antiproliferative agent is a CDK4/CDK6 inhibitor, such as pabociclib.

Embodiment 23. A method of preparing Compound FA or an amine salt thereof, the method comprising:

a) Reacting a tryptamine compound,

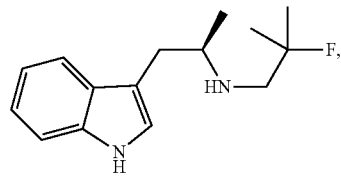 [SMILES: C[C@H](Cc1c[nH]c2ccccc12)NCC(C)(C)F]

or a salt thereof, with an aldehyde,

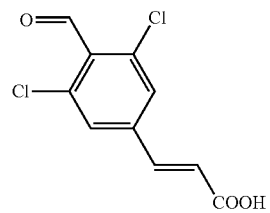 [SMILES: O=Cc1c(Cl)cc(/C=C/C(=O)O)cc1Cl]

or a salt thereof, under suitable conditions to form Compound FA

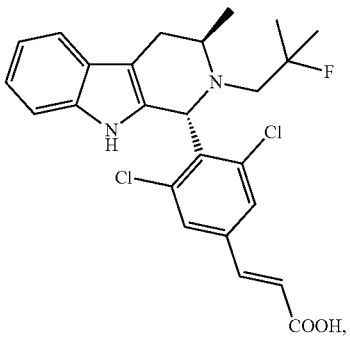 [SMILES: C[C@@H]1Cc2c([nH]c3ccccc23)[C@@H](c2c(Cl)cc(/C=C/C(=O)O)cc2Cl)N1CC(C)(C)F]

or a salt thereof;

b) Optionally converting Compound FA or a salt thereof into an amine salt of Compound FA.

Embodiment 24. The method of embodiment 23, wherein the amine salt is a diisopropylethyl amine salt, and the method comprises reacting Compound FA or a salt thereof with diisopropylethyl amine to provide the diisopropylethyl amine salt of Compound FA:

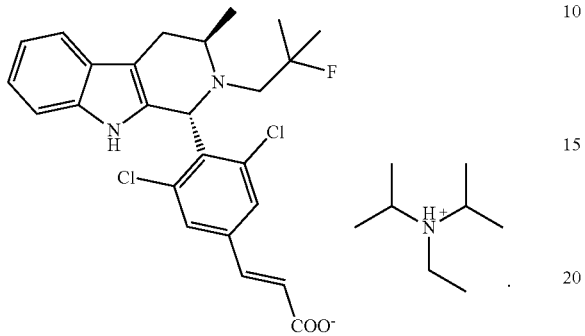

Embodiment 25. The method of embodiment 23, wherein the amine salt is a meglumine amine salt, and the method comprises reacting Compound FA or a salt thereof with meglumine to provide the meglumine salt of Compound FA:

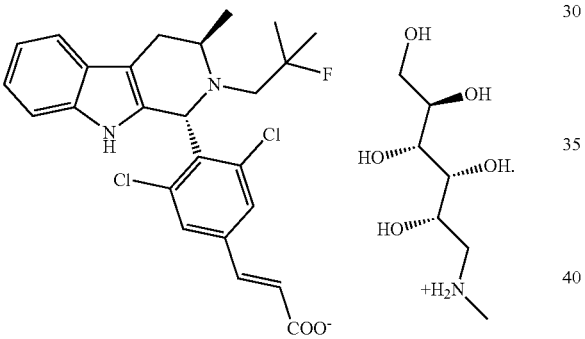

Embodiment 26. The method of embodiment 25, comprises reacting a diisopropylethyl amine salt of Compound FA with meglumine to provide the meglumine salt of Compound FA.

Embodiment 27. The method of any one of embodiments 23-26, wherein the tryptamine compound is prepared by a process comprising reacting

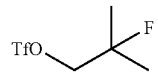

with

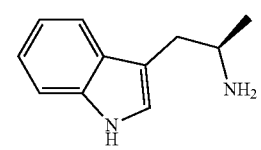

in the presence of a base.

Embodiment 28. The method of embodiment 27, wherein the

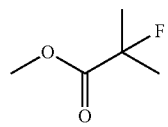

is prepared by a process comprising reducing

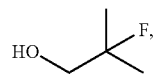

with a reducing agent to form an alcohol

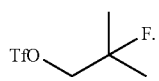

and subsequently reacting the alcohol with a triflate donor agent to form

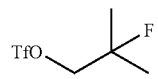

Embodiment 29. The method of embodiment 27, wherein the

is prepared by a process comprising reacting

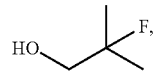

with a fluoride (e.g., HF/pyridine) to form an alcohol

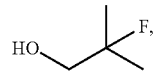

and subsequently reacting the alcohol with a triflate donor agent to form

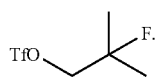

Embodiment 30. The method of any one of embodiments 23-29, wherein the aldehyde is prepared by a process comprising converting a dichloro-compound

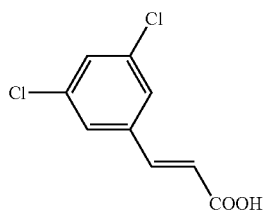 [SMILES: O=C(O)/C=C/c1cc(Cl)cc(Cl)c1]

into an anionic intermediate with a base, which is subsequently reacted with an aldehyde donor agent to form

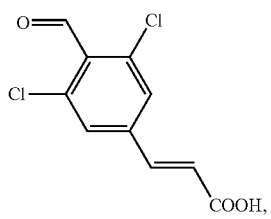 [SMILES: O=Cc1c(Cl)cc(/C=C/C(=O)O)cc1Cl]

or a salt thereof.

Definitions

Unless otherwise obvious from context, in any of the embodiments described herein, the compounds/salts herein can exist predominantly (e.g., at least 85%, at least 90%, at least 95%, at least 99%, etc.) in the stereoisomer as drawn, when applicable. For example, in some embodiments, Compound FA herein can have an enantiomeric purity of greater than 85% enantiomeric excess (e.g., greater than 90% ee, greater than 95% ee, or greater than 99% ee); in some embodiments, Compound FA herein can also have a diastereomeric purity of greater than 85% diastereomeric excess (e.g., greater than 90% de, greater than 95% de, or greater than 99% de); and in some embodiments, Compound FA herein can also have substantially E configuration with respect to the acrylic acid double bond, for example, with less than 1%, or non-detectable, Z configuration.

"Salt(s) of the present disclosure" as used herein refers to any salt of Compound FA described herein, preferably, an amine salt of Compound FA described herein, which can be in a solid form, such as one or more crystalline forms described herein (e.g., Form I, II, or III of meglumine salt of Compound FA or Form A of the lysine salt of Compound FA), amorphous form, or any mixture thereof, which can be anhydrous, hydrate, or solvate.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a salt of the present disclosure to a subject in need of such treatment.

The term "therapeutically effective amount," as used herein, refers to that amount of a therapeutic agent (e.g., any one or more of the salts of the present disclosure) sufficient to result in amelioration of one or more symptoms of a disorder or condition (e.g., breast cancer such as ER+ breast cancer), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

Example 1. General Methods

Materials: the starting materials, reagents, solvents, etc. are generally available through commercial sources.

$^1$H NMR was performed using Bruker Advance 300 equipped with automated sample (B-ACS 120).

POWDER X-RAY DIFFRACTION (XRPD): The solid samples were examined using X-ray diffractometer (Bruker D8 advance). The system is equipped with LynxEye detector. The x-ray wavelength is 1.5406 Å. The samples were scanned from 3 to 40° 2θ, at a step size 0.02° 2θ. The tube voltage and current were 40 KV and 40 mA, respectively.

Polarizing microscope analysis (PLM): PLM analysis was conducted on a Nikon Instruments Eclipse 80i. The image was captured by a DS camera and transmitted to the computer. The photo was processed with the NIS-Elements D3.0 software.

TGA ANALYSIS: TGA analysis was carried out on a TA Instruments TGA Q500. Samples were placed in an open tarred aluminum pan, automatically weighed, and inserted into the TGA furnace. The samples were heated at a rate of 10° C./min to final temperature.

DSC ANALYSIS: DSC analysis was conducted on a TA Instruments Q200. The calibration standard was indium. A sample in weight was placed into a TA DSC pan, and weight was accurately recorded. The samples were heated under nitrogen (50 ml/min) at a rate of 10° C./min to a final temperature.

Dynamic moisture sorption analysis (DVS): DVS was determined using IGAsorp (Hiden Isochema, UK). The sample was tested at a targeted RH (relative humidity) of 10 to 90% full cycle in step mode. The analysis was performed in 10% RH increments.

HPLC ANALYSIS: a representative HPLC method is shown below, which can be used, for example, to analyze the purity, solubility, and stability of the salts herein.

| | |
|---|---|
| Instrument | Agilent 1260 series |
| Column | Sunfire C18, 3.5 μm, 4.6*150 mm |
| Column temperature | 40° C. |
| Mobile phase | A: 0.05% TFA in H₂O, B: 0.05% TFA in Acetonitrile |
| Gradient condition (% of B) | 0-15 min: 15-85%, 15-25 min: 85% |
| Flow rate | 1.0 mL/min |
| Injection volume | 5 μL |
| UV wavelength | 220 nm |
| Post time | 5 min |

Example 2. Preparation of Meglumine (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylate

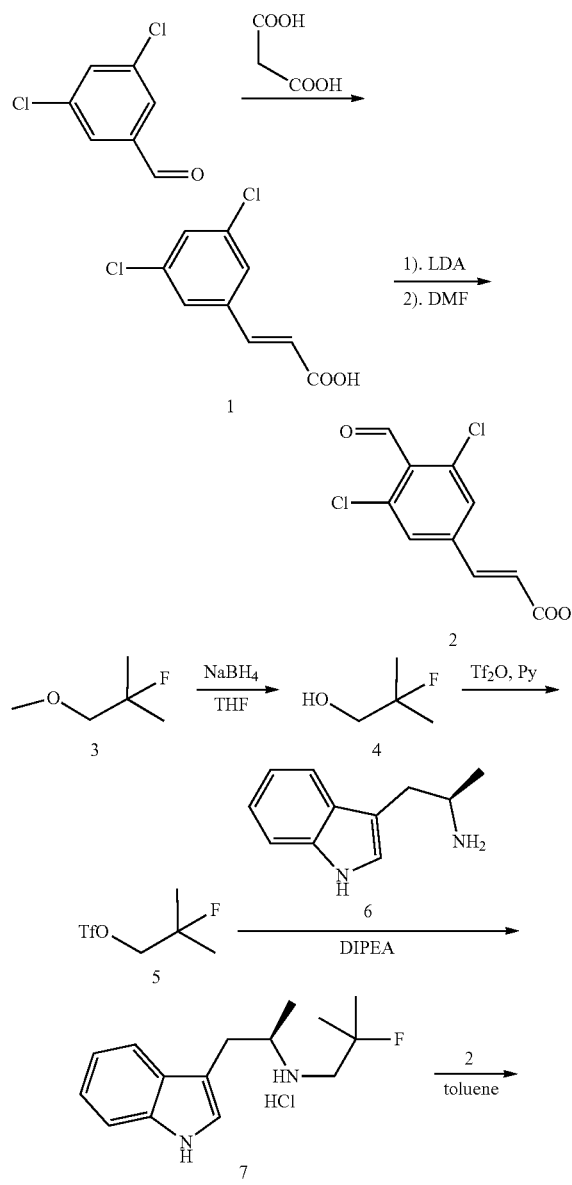

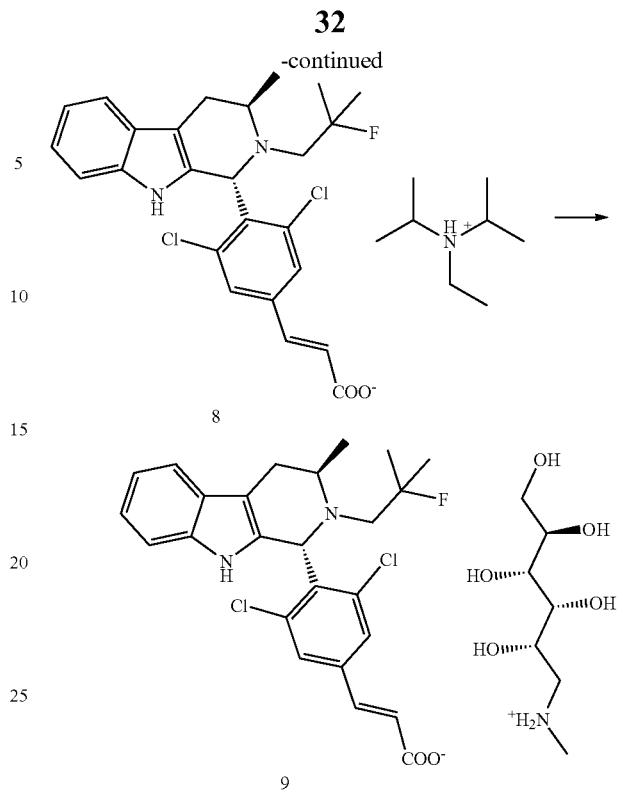

A mixture of 3,5-dichlorobenzaldehyde (250.0 g, 1.43 mol), malonic acid (223.0 g, 2.14 mol) and pyridine (250 mL) in DMF (500 mL) was heated at temperatures ranging from 30° C. to 75° C. until the reaction was completed. The mixture was then cooled to 10 to 20° C., and a hydrochloric acid solution (0.6 N, 5 L) was added. The mixture was stirred at 10 to 20° C. for 6 hours and filtered. The filter cake was washed with water, and dried at 40 to 60° C. under vacuum to produce 1 (281 g, 90% yield).

To a solution of 1 (50.0 g, 0.23 mol) in THF (1 L) was added LDA (2.0 M in THF, 290 mL) dropwise at −80 to −60° C. under N₂. The mixture was stirred at this temperature range for 0.5 hour, followed by slow addition of DMF (42.0 g, 0.58 mol). The resulting mixture was stirred at −70 to −50° C. until the reaction was completed. Water (10 mL) and hydrochloric acid (2.0 M, 900 mL) were added sequentially. The organic layer was separated, washed with an aqueous NaCl solution (5%, 250 mL) and concentrated to 200 mL. To the residue was added DCM (50 mL), and the resulting slurry was stirred at 20 to 30° C. for 6 hours and filtered. The filter cake was dried at 30 to 40° C. under vacuum to produce 2 (36.1 g, 64% yield).

To a suspension of NaBH₄ (16.5 g, 0.44 mol) in THF (120 mL) was added 3 (40.0 g, 0.33 mol) in several portions maintaining the reaction temperature at 35 to 45° C. under N₂. The mixture was stirred at 35 to 45° C. until the reaction was completed. An aqueous KHCO₃ solution (20%, 80 L) and DCM (400 mL) were added, and the resulting mixture was filtered. The organic layer was separated, washed with aqueous NaCl (20%, 200 mL), dried over 4 Å molecular sieves (24 g) and filtered to produce a solution of crude 4 in DCM. To the solution of 4 in DCM was added pyridine (52.7 g, 0.67 mol), followed by slow addition of Tf₂O (98.7 g, 0.35 mol) maintaining the reaction temperatures at −10 to 0° C. The mixture was stirred at 0 to 10° C. until the reaction was completed. Water (400 mL) was added, and the organic layer was separated, washed with aqueous NaHCO₃ (6.5%, 400 mL) and aqueous NaCl (20%, 200 mL) solutions sequentially, and concentrated to produce 5 (57.7 g, 78% yield).

To a solution of 6 (20.0 g, 0.115 mol) and DIPEA (19.3 g, 0.149 mol) in MeCN (200 mL) was added 5 (40.0 g, 0.178 mol), and the mixture was heated at 65 to 75° C. under N₂ until the reaction was completed. The reaction mixture was concentrated at 20 to 30° C. under vacuum, followed by addition of EtOAc (300 mL). The resulting mixture was washed with an aqueous NaHCO₃ solution (6.5%, 200 L), water (2×100 L), and concentrated. To the crude residue was added MeCN (40 mL) and EtOAc (20 mL), followed by a hydrogen chloride solution (4.0 M in EtOAc, 40 mL) at −5 to 5° C. The mixture was stirred at −5 to 5° C. for 8 hours and filtered. The filter cake was washed with EtOAc (65 L), and dried at 50 to 65° C. under vacuum to produce 7 (23.9 g, 73% yield).

To a suspension of 7 (12.8 g, 0.045 mol) in toluene (250 mL) was added an aqueous Na₂CO₃ solution (13%, 208 g), and the mixture was stirred for 0.5 hour. The organic layer was separated. To the organic layer was added DIPEA (3.64 g) and 2 (10 g, 0.041 mol), and the mixture was heated at 100 to 120° C. under N₂ until the reaction was completed. The mixture was cooled to 45-55° C., followed by addition of seed crystals of 8 and EtOAc (200 mL). A solvent switch from toluene to EtOAc was performed by distillation with additional amounts of EtOAc (2×250 mL) to a slurry, followed by addition of DIPEA (5.2 g). The slurry was stirred at 15 to 25° C. for 12 hours and filtered. The filtered cake was washed with a mixed solvent of EtOAc (28 mL) and toluene (12 mL), and dried at 35 to 45° C. under vacuum to produce 8 (18.0 g, 73% yield).

To a suspension of 8 (17.5 g, 0.029 mol) in EtOAc (315 mL) was added an aqueous citric acid solution (1.5%, 226 mL). The mixture was stirred for 1 hour, and the layers were separated. The organic layer was washed with an aqueous citric acid solution (0.1%, 262 mL), water (2×175 mL), and concentrated to a low volume of 35 mL. To the concentrate was added methanol (210 mL), followed by an aqueous meglumine solution (20%, 26.2 g) and seed crystals of 9. The mixture was stirred at 15 to 25° C. for 2 hours, and then additional amount of the aqueous meglumine solution (20%, 8.8 g) was added. The mixture was then stirred at 15 to 25° C. for 16 hours and filtered. The filtered cake was washed with a mixed solution of MeOH and water (6:1, 70 mL), and dried at 46 to 65° C. under vacuum to produce 9 (15.2 g, 78% yield), which is in crystalline Form I. HRMS System showed ion peak of [M+H]⁺: m/z 475.1348.

The following table shows the proton NMR and its assignments of 9:

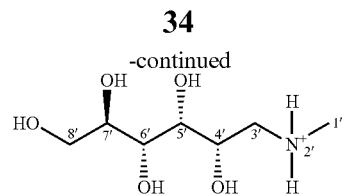

| Chemical Shift (δ) ppm* | Multiplicity† | Approximate integration # of proton | Assignment or resonance # |
|---|---|---|---|
| 10.38 | s | 1H | NH-1 |
| 7.79 | d (J = 1.2 Hz) | 1H | H-21/23 |
| 7.52 | brs | 1H | H-23/21 |
| 7.39 | d (J = 7.2 Hz) | 1H | H-5 |
| 7.24 | d (J = 16.0 Hz) | 1H | H-25 |
| 7.16 | d (J = 8.0 Hz) | 1H | H-8 |
| 6.97 | td (J = 7.2, 1.2 Hz) | 1H | H-7 |
| 6.92 | td (J = 7.2, 1.2 Hz) | 1H | H-6 |
| 6.59 | d (J = 16.0 Hz) | 1H | H-26 |
| 5.58 | s | 1H | H-14 |
| 3.86 | m | 1H | H-4' |
| 3.72 | t (J = 5.2 Hz) | 1H | H-11 |
| 3.67 | dd (J = 5.2, 1.2 Hz) | 1H | H-5' |
| 3.59 | dd (J = 10.8, 3.2 Hz) | 1H | H-8'a |
| 3.50 | m | 1H | H-6' |
| 3.43 | overlap | 1H | H-7' |
| 3.40 | t (J = 5.2 Hz) | 1H | H-8'b |
| 3.08 | brd (J = 14.4 Hz) | 1H | H-10a |
| 2.96 | overlap | 1H | H-15a |
| 2.95 | overlap | 1H | H-3'a |
| 2.85 | dd (J = 12.4, 8.4 Hz) | 1H | H-3'b |
| 2.63 | d (J = 14.4 Hz) | 1H | H-10b |
| 2.47 | s | 3H | H-1' |
| 2.23 | dd (J = 29.2, 14.4 Hz) | 1H | H-15b |
| 1.13 | d (J = 21.6 Hz) | 3H | H-17/18 |
| 1.10 | d (J = 21.6 Hz) | 3H | H-18/17 |
| 1.05 | d (J = 6.4 Hz) | 3H | H-12 |

*Referenced to DMSO-d₆ at δ = 2.50 ppm
†s: singlet; d: doublet; t: triplet; m: multiplet; dd: double doublet; td: triple doublet; brs: broad singlet; brd: broad doublet Procedure of preparing seed crystals of 8: To a suspension of 7 (128 g, 0.45 mol) in toluene (2.5 L) was added an aqueous Na₂CO₃ solution (13%, 2080 g), and the mixture was stirred for 0.5 hour. The organic layer was separated. To the organic layer was added DIPEA (36.4 g) and 2 (100 g, 0.41 mol), and the mixture was heated at 100 to 120° C. under N₂ until the reaction was completed. The mixture was cooled to 45-55° C. Distillation of toluene was performed with additional amounts of EtOAc (2×2.5 L) to a slurry, followed by addition of DIPEA (52 g). The slurry was stirred at 15 to 25° C. for no less than 12 hours and filtered. The filtered cake was washed with a mixture of EtOAc (280 mL) and toluene (120 mL), and dried at 35 to 45° C. under vacuum to produce 8 (180.5 g, 73% yield) used as seed crystals. Representative XRPD and DSC spectra of the crystal form 8 are shown in FIGS. 8A and 8B.

Procedure of preparing seed crystals of 9: To a suspension of 8 (8.7 g, 0.014 mol) in EtOAc (157 mL) was added an aqueous citric acid solution (1.5%, 112 mL). The mixture was stirred for 1 hour, and the layers were separated. The organic layer was washed with an aqueous citric acid solution (0.1%, 130 mL), water (2×87 mL), and concentrated to a low volume of about 17 mL. To the concentrate was added methanol (104 mL), followed by an aqueous meglumine solution (20%, 13.0 g). The mixture was stirred at 15 to 25° C. for 2 hours, and then additional amount of the aqueous meglumine solution (20%, 4.4 g) was added. The mixture was then stirred at 15 to 25° C. for no less than 16 hours and filtered. The filtered cake was washed with a mixture of MeOH and water (6:1, 35 mL), and dried at 46 to 65° C. under vacuum to produce 9 (7.6 g, 78% yield) used as seed crystals (Form I).

Example 3. Alternative Method for the Preparation of 2-fluoro-2-methylpropan-1-ol

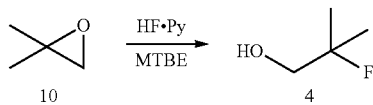

A solution of 10 (1.0 eq) in MTBE (10 V) under $N_2$ was cooled to $-20°$ C.$\pm 5°$ C. Olah's reagent (2.0 eq.) was added dropwise to the system and the temperature of the mixture was kept below $-10°$ C. After the addition, the reaction was warmed to 25° C.$\pm 5°$ C., and stirred at the same temperature until the reaction was completed. $H_2O$ (10 V) was added slowly to the reaction. The organic layer was separated, washed with a saturated $NaHCO_3$ (3 V) solution and brine (3 V), and then dried over $MgSO_4$. After filtration, the filtrate was concentrated to afford the desired alcohol 4 as a light-yellow liquid, which was used for next step without further purification.

Example 4. Solid State Characterization of Compound FA, (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid Procedure for preparing Compound FA: To a suspension of 7 (33.4 g, 0.12 mol) (see Example 2) in toluene (575 mL) was added an aqueous $Na_2CO_3$ solution (13%, 540 g), and the mixture was stirred for 0.5 hour. The layers were separated. To the organic layer was added 2 (25 g, 0.10 mol) (see Example 2), and the mixture was heated at 100 to 120° C. under $N_2$ until the reaction was completed. The mixture was concentrated to about 25 mL, followed by addition of MTBE (250 mL) and heptane (250 mL), and filtered. The filter cake was dried at 35 to 45° C. under vacuum to produce compound FA (30.6 g, 64% yield).

This example analyzes the solid state of Compound FA obtained above by $^1H$ NMR, LCMS, XRPD, PLM, TGA, DSC and DVS.

$^1H$ NMR and TGA profiles showed that there was residual solvent. XRPD pattern and PLM photo showed that the sample was crystalline with low crystallinity. The purity, as analyzed by LCMS, was 97.11% (254 nm, percent area). In TGA profile, there was about 1.58% and 2.39% weight loss prior to decomposition. An endothermic peak with onset temperature of 142.17° C. was observed in DSC profile. Based on such, the sample should be a solvate. Representative XRPD and DSC spectra are shown in FIGS. 7A and 7B, respectively.

DVS result showed that it adsorbed about 1.7% moisture at 80% RH. After DVS test, XRPD pattern of the sample didn't change. See FIG. 7A.

Example 5. Salt Screening

Salt screening of Compound FA was conducted with 15 acids and 10 bases in 96-well plate using 12 solvents. Salts could not be formed with 15 acids, but with several bases including NaOH, KOH, L-arginine, L-lysine, ammonia, meglumine and choline hydroxide. The 15 acids tested were Hydrochloric acid, Phosphoric acid, Sulfuric acid, L-Tartaric acid, Hydrobromic acid, Fumaric acid, p-Toluenesulfonic acid, Citric acid, Methanesulfonic acid, Benzoic acid, Benzenesulfonic acid, Succinic acid, Maleic acid, L-lactic acid, and Malonic acid. The base tested were NaOH, KOH, L-arginine, L-lysine, Ammonia, Nicotinamide, Meglumine, Tromethamine, Choline hydroxide, and Glutamine. The solvents tested in the screening experiments were Methanol, ACN, Ethanol, MTBE, IPA, Acetone, 2-butanone, Water, Isobutanol, EtOAC, THF, and Isopropyl acetate.

Briefly, for the acids, appropriate amount of 15 acids were dissolved with methanol to make a solution with the concentration of 0.1 M. About 420 mg of Compound FA was dissolved in methanol to make a solution with the concentration of 30 mg/mL. The Compound FA solution was then distributed into 15*8 wells of 96-well plates. Each well contained 100 μL of compound FA solution. 65 μL of each acid solution was added into each row, except $H_2SO_4$ acid was 32.5 μL. After dryness, 200 μL of 8 test solvents were added to column 1-8 of the row A-O. Wells were covered with a film with pinhole and evaporated in an operating laboratory fume hood under ambient conditions. Some solid samples obtained were analyzed by)(RFD, $^1H$ NMR etc.

For the bases, appropriate amount of 10 bases were dissolved with methanol or the mixture of methanol and water to make a solution with the concentration of 0.1 M. Appropriate amount of Compound FA was dissolved with acetone to make a solution with the concentration of 30 mg/mL. Compound FA solution was then distributed into 10*12 wells of 96-well plates. Each well contained 100 μL of Compound FA solution. 65 μL of each base solution was added into each row. After dryness, 200 μL of 12 solvents were added to column 1-12 of 10 rows. Wells were covered with a film with pinhole, protected from light, and evaporated under $N_2$ conditions. Some solid samples obtained were determined by XRPD and $^1H$ NMR.

Results of Salt Screening Using Acids

After dry, most samples in 96-well plate were sticky or glassy. No solid appeared in row F, G, I and L. Solid samples were analyzed by XRPD and $^1H$ NMR. F1, G1, 18 and L5 were also analyzed by $^1H$ NMR. Compared with Compound FA, there was no chemical shift changes in all $^1H$ NMR profiles. It was thus concluded that under the tested conditions, Compound FA could not form salt with all 15 acids.

Results of Salt Screening Using Bases 10 bases were used for salt screening of Compound FA in 96-well plate. After dry, solid sample appeared in Row C, D, F, H and K. Samples in Row A and B was glassy. In row E, and G, all wells were glassy, except E10 and G10 were semisolid. In row L, all wells were glassy or oil, except L10 was the mixture of yellow and white powder.

Solid samples were analyzed by XRPD and one sample in each row was analyzed by NMR. Results showed that Compound FA formed salt with NaOH, KOH, L-arginine, L-lysine, ammonia, meglumine, tromethamine, and choline hydroxide.

According to the initial result of 96-well plate screening in Example 5, small scale-ups with 9 bases with Compound FA were tested. L-lysine salt and meglumine salt were obtained, which were subsequently scaled up for solubility and stability studies (see Example 7). The solid form obtained for meglumine salt was further studied in polymorph screening, see Example 6. Under the small scale-up conditions, no crystalline solid were obtained with L-arginine, ammonia, $MgCl_2$ and $CaCl_2$). Compound FA formed salt with tromethamine, choline hydroxide, both of which appeared to be solvate (see Examples 8 and 9). Compound FA did not form salt with glutamine under the conditions tested.

Example 6. Meglumine Salt of Compound FA Polymorphs and Interconversion

Meglumine salt of Compound FA was prepared and used as initial material (Form I) for polymorph screening. Screening was conducted using single and binary solvent mixtures by various crystallization methods, such as solvent crystallization, precipitation, slurry, evaporation and diffusion method. Thermal and mechanical treatments were also performed to explore additional crystal form.

Solid samples obtained were characterized by X-ray powder diffractermeter (XRPD), differential scanning calorimeter (DSC), thermogravimetric analyzer (TGA) and polarized microscopy (PLM).

Two crystal forms (Form I, II) and dihydrate were identified and prepared in the screening. Interconversion studies of different forms and dihyate were performed in water and IPA at room temperature and 60° C. Results showed that dihydrate was the most stable in water at room temperature, and Form I was the most stable crystal form in IPA (room temperature and 60° C.) and in water at 60° C. In addition, crystal form of Form I remained unchanged after storage at 92.5% RH for 10 days.

Example 6A. Form I of the Meglumine Salt

Preparation of Form I: 1.08536 g of meglumine was added into 50 mL of methanol with stirring at room temperature. The solid sample was almost dissolved after added another 30 mL of methanol with stirred for 20 min. Added 2.6 g of Compound FA, and then the solution became clear. Precipitation occurred 25 min later. The suspension was concentrated to dry after 1 h. Added 20 mL of IPA and kept stirring at room temperature overnight. Then added 30 mL of IPA and stirred for 2 hours. The sample was collected by filtration. After characterization, the sample was used as initial material for polymorph screening.

Physical treatment of Form I: Form I of meglumine salt was grinded for 2 min and 5 min. After grinding, the crystallinity declined, but the crystal form was still Form I.

Characterization of Form I: The sample was rodlike crystal. TGA and DSC profiles showed that there was about 0.2% weight loss prior to decomposition, and an endothermic peak with onset temperature of 224.83° C. The sample was named as Form I. Representative XRPD and DSC spectra are shown in FIGS. 1A-1B. A table of XRPD peaks are shown below in Table 1

TABLE 1

XRPD peak tables for Form I.

| Angle 2-Theta ° | Intensity % | d value Angstrom | Intensity Count |
|---|---|---|---|
| 4.705 | 58.5 | 18.76671 | 1235 |
| 9.054 | 45.8 | 9.7593 | 966 |
| 9.95 | 85.4 | 8.88233 | 1802 |
| 10.248 | 11.9 | 8.62498 | 252 |
| 11.02 | 16.5 | 8.02203 | 349 |
| 11.288 | 22 | 7.83245 | 464 |
| 12.234 | 8.9 | 7.22857 | 187 |
| 12.915 | 23.9 | 6.84911 | 505 |
| 13.28 | 28.7 | 6.66177 | 605 |
| 13.493 | 22.3 | 6.55701 | 471 |
| 13.761 | 9.9 | 6.43003 | 209 |
| 14.136 | 19.1 | 6.2604 | 402 |
| 14.746 | 7.4 | 6.00253 | 157 |
| 15.077 | 20.9 | 5.87157 | 441 |
| 15.517 | 6.6 | 5.70587 | 140 |
| 16.352 | 28.9 | 5.41663 | 609 |
| 16.741 | 12.7 | 5.29152 | 268 |
| 17.579 | 76.7 | 5.04099 | 1618 |
| 18.22 | 38.7 | 4.86526 | 817 |
| 18.776 | 27.5 | 4.72233 | 581 |
| 18.967 | 53.4 | 4.67508 | 1127 |
| 19.431 | 10.5 | 4.56456 | 222 |
| 20.018 | 29.7 | 4.43201 | 627 |
| 20.383 | 20.9 | 4.35348 | 440 |
| 20.981 | 18.9 | 4.23083 | 398 |
| 21.52 | 100 | 4.1259 | 2110 |
| 22.039 | 13.4 | 4.0299 | 283 |
| 22.415 | 23.4 | 3.96315 | 494 |
| 23.268 | 18.8 | 3.81976 | 397 |
| 23.654 | 40.8 | 3.75832 | 860 |
| 23.916 | 20.4 | 3.7177 | 431 |
| 24.292 | 11.1 | 3.66101 | 235 |
| 24.886 | 23.6 | 3.57504 | 499 |
| 25.312 | 22.8 | 3.51577 | 481 |
| 26.296 | 18 | 3.38644 | 379 |
| 26.592 | 8.2 | 3.34944 | 172 |
| 26.91 | 10.1 | 3.31058 | 214 |
| 27.226 | 12.8 | 3.27283 | 271 |
| 27.755 | 9.4 | 3.21163 | 198 |
| 28.466 | 15.3 | 3.13302 | 323 |
| 28.786 | 9.5 | 3.09887 | 201 |
| 29.319 | 14.6 | 3.04379 | 308 |
| 29.64 | 11.3 | 3.01158 | 239 |
| 30.037 | 13.8 | 2.9726 | 291 |
| 30.86 | 6 | 2.8952 | 127 |
| 31.481 | 11.8 | 2.83946 | 250 |
| 31.828 | 8.9 | 2.80933 | 188 |
| 32.39 | 7.3 | 2.76183 | 155 |
| 32.861 | 9 | 2.72333 | 189 |
| 33.054 | 12.6 | 2.70787 | 265 |
| 33.805 | 10.6 | 2.64942 | 223 |
| 34.238 | 10.4 | 2.61686 | 219 |
| 34.839 | 8.6 | 2.57311 | 181 |
| 35.157 | 8.4 | 2.55054 | 178 |
| 35.936 | 13.3 | 2.49704 | 280 |
| 36.318 | 12.4 | 2.47168 | 261 |
| 36.924 | 14.6 | 2.43245 | 309 |
| 37.393 | 18.6 | 2.40304 | 393 |
| 37.683 | 11.8 | 2.38516 | 248 |
| 38.563 | 7.7 | 2.33274 | 162 |

Example 6B. Form III of Meglumine Salt Form

Preparation of dihydrate: About 60 mg of meglumine salt (Form I) was dissolved in 3 mL of methanol with stirring at 60° C. Added 6 mL of water and kept stirring for 30 min at 60° C. The clear solution was cooled slowly to room temperature and kept stirring at room temperature overnight. No precipitation occurred. Added 1 mL of water and stirred overnight again, solid sample appeared and was collected by filtration. After drying at 40° C. for 4 h, XRPD showed that most of the sample became anhydrous (Form II). Stirred in water for 30 min and dried at room temperature, dihydrate was prepared.

Alternatively, the dihydrate form can be prepared by using solvent/antisolvent precipitation method. For example, about 20 mg of meglumine salt was dissolved in 1 mL of methanol with stirring at 60° C. Added 2 mL of water, and kept stirring at 60° C. for 20 min. Cooled slowly to room temperature. The solution is clear at first. Precipitation occurred after stirred at room temperature overnight. The crystalline form obtained from this precipitation is dihydrate.

The sample was tested by XRPD, TGA and DSC. There was about 6.824% weight loss prior to decomposition. In DSC profile, there were two endothermic peaks with onset temperature of 63.4° C. and 176.4° C., respectively.

Characterization of Dihydrate: Representative XRPD and DSC spectra are shown in FIGS. 3A-3B. A table of XRPD peaks are shown below in Table 2.

TABLE 2

Table of XRPD Peaks for Dihydrate Meglumine Salt

| Angle 2-Theta ° | Intensity % | d value Angstrom | Intensity Count |
|---|---|---|---|
| 3.682 | 46.2 | 23.9776 | 549 |
| 6.401 | 23.4 | 13.79821 | 278 |
| 7.46 | 46.4 | 11.84147 | 551 |
| 10.245 | 68.5 | 8.62762 | 814 |
| 11.216 | 22.7 | 7.88285 | 270 |
| 11.969 | 51.3 | 7.38831 | 609 |
| 14.463 | 100 | 6.11939 | 1188 |
| 14.975 | 14.6 | 5.91139 | 173 |
| 15.552 | 37.5 | 5.69327 | 446 |
| 16.691 | 16.7 | 5.3072 | 198 |
| 16.968 | 31.3 | 5.22105 | 372 |
| 17.357 | 51.5 | 5.10515 | 612 |
| 17.777 | 26.8 | 4.98523 | 318 |
| 18.751 | 12.6 | 4.72849 | 150 |
| 19.181 | 51.7 | 4.62345 | 614 |
| 19.714 | 39.4 | 4.49964 | 468 |
| 20.294 | 27.5 | 4.3723 | 327 |
| 20.559 | 49.3 | 4.31661 | 586 |
| 21.084 | 17.3 | 4.21037 | 205 |
| 21.542 | 31.2 | 4.12184 | 371 |
| 21.967 | 97.2 | 4.04296 | 1155 |
| 22.501 | 50.3 | 3.94828 | 597 |
| 22.794 | 21.5 | 3.8982 | 255 |
| 23.761 | 37 | 3.74163 | 439 |
| 24.606 | 46.5 | 3.615 | 552 |
| 24.946 | 32 | 3.56653 | 380 |
| 25.503 | 20.7 | 3.48992 | 246 |
| 25.876 | 22.3 | 3.44047 | 265 |
| 26.501 | 21.7 | 3.36075 | 258 |
| 27.65 | 14.1 | 3.2236 | 168 |
| 28.078 | 30.8 | 3.17543 | 366 |
| 28.96 | 14.7 | 3.08069 | 175 |
| 29.792 | 13 | 2.99655 | 155 |
| 30.134 | 15.2 | 2.96333 | 181 |
| 30.851 | 22.4 | 2.89604 | 266 |
| 31.433 | 21.4 | 2.84373 | 254 |
| 32.22 | 14.1 | 2.776 | 168 |
| 32.853 | 15.7 | 2.724 | 187 |
| 33.07 | 18.9 | 2.70662 | 225 |
| 35.162 | 15.1 | 2.55018 | 179 |
| 35.587 | 19.4 | 2.52074 | 231 |
| 37.364 | 12 | 2.40479 | 143 |
| 38.134 | 16.8 | 2.35803 | 200 |
| 39.32 | 15.9 | 2.28955 | 189 |

Example 6C. Form II of the Meglumine Salt

Preparation of Form II: The dihydrate prepared above was dried at 60° C. for 5 h and 40° C. overnight. The sample was tested by XRPD, TGA and DSC immediately. XRPD pattern of the dry sample was different from Form I and dihydrate (FIG. 2A). Determined by TGA and DSC, there were no weight loss prior to decomposition, and two endothermic peaks in DSC profile (FIG. 2B). The melting of sample was 174.13° C. The small endothermic peak with onset temperature of 43.41 and enthalpy of 3.999 J/g should be the peak of desolvation. Little water should be adsorbed during DSC testing. The sample with the melting of 174.13° C. was named as Form II. The sample was used for interconversion studies.

Characterization of Form II: Representative XRPD and DSC spectra are shown in FIGS. 2A-2B. A table of XRPD peaks are shown below in Table 3.

TABLE 3

XRPD Peaks for Form II

| Angle 2-Theta ° | Intensity % | d value Angstrom | Intensity Count |
|---|---|---|---|
| 3.997 | 34.8 | 22.08663 | 577 |
| 7.569 | 16.1 | 11.67003 | 267 |
| 7.983 | 87.7 | 11.0666 | 1456 |
| 10.257 | 24.2 | 8.61696 | 402 |
| 11.247 | 13.8 | 7.86115 | 229 |
| 11.956 | 83.5 | 7.39632 | 1386 |
| 12.351 | 46.3 | 7.16088 | 769 |
| 13.095 | 15.1 | 6.75554 | 250 |
| 14.666 | 28.2 | 6.03523 | 468 |
| 14.896 | 20.7 | 5.94248 | 344 |
| 15.541 | 27.2 | 5.69708 | 451 |
| 16.145 | 37.3 | 5.48558 | 619 |
| 17.22 | 34 | 5.14533 | 564 |
| 17.791 | 9.2 | 4.98143 | 153 |
| 18.544 | 12.8 | 4.78076 | 213 |
| 18.944 | 15.2 | 4.68083 | 253 |
| 19.327 | 17.5 | 4.58881 | 290 |
| 19.653 | 43.4 | 4.51344 | 720 |
| 19.938 | 19.4 | 4.44964 | 322 |
| 20.515 | 17 | 4.32574 | 283 |
| 20.831 | 26.1 | 4.26092 | 433 |
| 22.072 | 40.2 | 4.02395 | 667 |
| 22.528 | 100 | 3.94362 | 1660 |
| 23.235 | 13.9 | 3.82509 | 230 |
| 23.885 | 33.4 | 3.72254 | 554 |
| 24.527 | 19.5 | 3.62652 | 324 |
| 24.836 | 20.2 | 3.58213 | 336 |
| 25.695 | 12.5 | 3.4643 | 208 |
| 26.285 | 22.3 | 3.38783 | 371 |
| 27.049 | 10.8 | 3.29385 | 179 |
| 28.003 | 16.3 | 3.18375 | 270 |
| 29.16 | 12.7 | 3.06002 | 210 |
| 29.549 | 10.7 | 3.02064 | 177 |
| 30.185 | 9.9 | 2.9584 | 165 |
| 30.707 | 19 | 2.90925 | 316 |
| 32.769 | 18.1 | 2.73077 | 301 |
| 33.724 | 10.2 | 2.6556 | 170 |
| 34.299 | 9.8 | 2.61235 | 163 |
| 35.256 | 12 | 2.54361 | 200 |
| 35.458 | 10.5 | 2.5296 | 174 |
| 37.221 | 10.9 | 2.41372 | 181 |
| 38.178 | 11.4 | 2.3554 | 190 |
| 39.46 | 10.2 | 2.28177 | 170 |

Example 6D. Meglumine Salt Form Interconversion Study

Interconversion study: Interconversion studies were carried out by mixing the same amount of different form solids in IPA or water, respectively. Suspensions were kept stirring at room temperature and 60° C. for several days, during which suspensions were filtrated and analyzed by XRPD.

Eight conditions with different substances, temperature and solvents were used for interconversion study. Results showed that dihydrate was the most stable crystal form in water at room temperature, and Form I was the most stable crystal form in water at 60° C. and IPA.

All conditions and results were listed in Table 4.

TABLE 4

Results of interconversion study.

| Substances | Solvent | Temperature | Final crystal form |
|---|---|---|---|
| Form I, Dihydrate | Water | 25° C. | Dihydrate |
|  |  | 60° C. | Form I |
|  | IPA | 25° C. | Form I |
|  |  | 60° C. | Form I |
| Form I, | Water | 25° C. | Dihydrate |
| Form II, Dihydrate | IPA | 25° C. | Form I |
| Form I | Water | 25° C. | Dihydrate |
| Form I | Water | 60° C. | Form I |

Example 6E. Meglumine Salt Form Stability Study

Solid stability test of Form I at 92.5% RH for 10 days: About 20 mg of meglumine salt Form I was put into the condition of 25° C./92.5% RH for 10 days. At 10 days, the sample was analyzed by XRPD.

Result showed that the Form I of meglumine salt remained unchanged after 10 days.

Figure 1C:
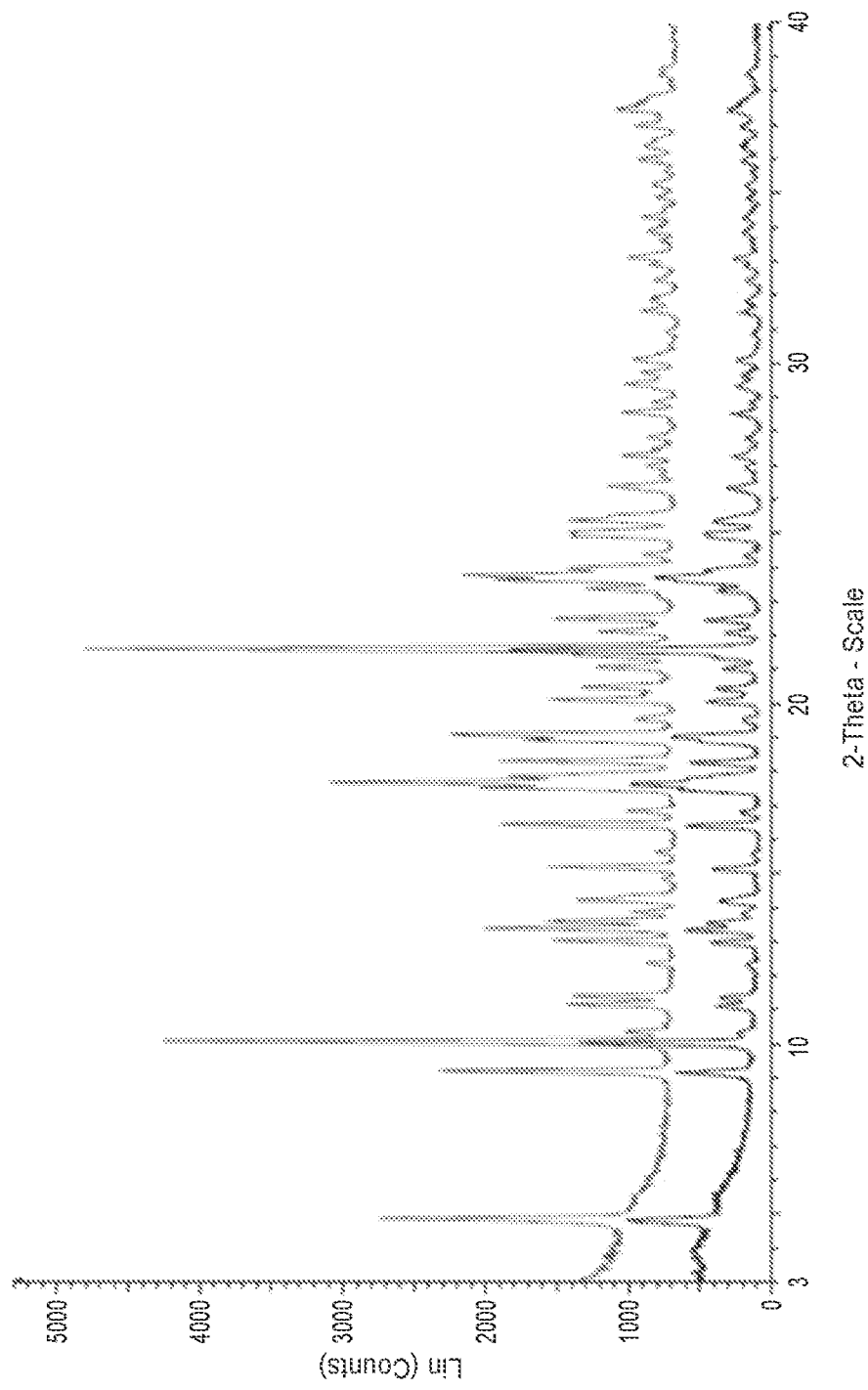

Representative XRPD patterns were shown in FIG. 1C.

Conclusion Meglumine salt of Compound FA solid state was prepared and used as initial material (Form I) for polymorph screening. Two crystal forms (Form I, II) and dihydrate were identified and prepared in the screening. Interconversion studies of different forms and dihydrate were performed in water and IPA at room temperature or 60° C. Results showed that dihydrate was the most stable in water at room temperature, and Form I was the most stable in IPA (room temperature and 60° C.) and in water at 60° C. In addition, Form I of meglumine salt remained unchanged after storage at 92.5% RH for 10 days.

Example 7. Preparation of L-Lysine Salt and Meglumine Salt for Solubility and Stability Test Lysine Salt: 239.8 mg of Compound FA was dissolved in 4.5 mL of isobutanol at 50° C. with stirring. 0.52 mL of 1 M L-lysine/water solution was added. Precipitation occurred about 15 min later. The reaction was kept stirring at 50° C. for about 1 hour. Cooled to room temperature, the solid sample was collected by filtration and dry under vacuum at 60° C. overnight. This lysine salt obtained is Form A. Representative XRPD and DSC spectra are shown in FIGS. 4A-4B. A table of XRPD peaks are shown below in Table 5.

TABLE 5

XRPD peaks of L-lysine salt in Form A

| Angle 2-Theta ° | Intensity % | d value Angstrom | Intensity Count |
|---|---|---|---|
| 4.172 | 46.4 | 21.16375 | 982 |
| 8.357 | 14.4 | 10.57154 | 304 |
| 10.151 | 100 | 8.70741 | 2117 |
| 11.06 | 29 | 7.99305 | 613 |
| 12.525 | 19.1 | 7.06178 | 405 |
| 13.007 | 49.5 | 6.80083 | 1047 |
| 13.301 | 20.2 | 6.65135 | 428 |
| 14.6 | 15.8 | 6.06208 | 335 |
| 15.128 | 7.7 | 5.85202 | 163 |
| 15.963 | 10.1 | 5.54746 | 214 |
| 16.33 | 11.9 | 5.42356 | 252 |
| 16.688 | 7.8 | 5.30809 | 165 |
| 16.964 | 10.6 | 5.22235 | 224 |
| 19.111 | 12 | 4.64034 | 255 |
| 19.404 | 48.1 | 4.57085 | 1018 |
| 20.383 | 18.2 | 4.35342 | 386 |
| 20.896 | 44.6 | 4.24784 | 944 |
| 22.231 | 37 | 3.99555 | 783 |
| 22.427 | 31.7 | 3.96111 | 671 |
| 22.948 | 67.7 | 3.87243 | 1434 |
| 23.428 | 15.3 | 3.79408 | 324 |
| 24.612 | 19.8 | 3.61413 | 419 |
| 26.451 | 11 | 3.36687 | 233 |
| 26.757 | 7.2 | 3.32907 | 152 |
| 27.422 | 5.5 | 3.24985 | 117 |
| 28.811 | 10.6 | 3.09629 | 225 |
| 29.442 | 7 | 3.03135 | 148 |
| 29.733 | 7.7 | 3.0023 | 162 |
| 30.754 | 10 | 2.90496 | 211 |
| 31.72 | 22.8 | 2.8186 | 483 |
| 32.203 | 7.3 | 2.77742 | 154 |
| 32.598 | 8.5 | 2.74471 | 179 |
| 32.731 | 8.7 | 2.73387 | 185 |
| 33.038 | 10.3 | 2.70915 | 219 |
| 33.799 | 7.7 | 2.64987 | 163 |
| 35.15 | 5.4 | 2.55105 | 114 |
| 35.545 | 5.4 | 2.52357 | 115 |
| 36.475 | 8.1 | 2.46133 | 171 |
| 37.212 | 5.7 | 2.41431 | 120 |
| 37.717 | 5.8 | 2.38309 | 123 |

Meglumine Salt: 237.92 mg of Compound FA was dissolved in 5 mL of IPA at room temperature with stirring. Then 10 mL of 0.05 M meglumine/methanol solution was added. Precipitation occurred about 25 min later. The reaction was kept stirring at room temperature for 3 hours. The solid sample was obtained by filtration and dry under vacuum at 60° C. overnight. Analysis shows that the meglumine salt obtained is Form I.

For solubility test: About 20 mg of Compound FA, L-lysine salt and meglumine salt (Form I) were weighed into vials, added 3 mL of pH1.2 or pH 6.8 buffer to make saturated solutions. All suspensions were kept shaking with 200 rpm at room temperature for up to 24 hours. At 30 min and 24 hours, the sample solution was filtered and analyzed by HPLC to determine the solubility. At 24 hours, remaining solids were collected and determined by XRPD.

For stability test: About 20 mg of Compound FA, L-lysine salt and meglumine salt (Form I) were weighed into vials, and put at the condition of 40° C./75% RH for 8 days. At 0 and 8 days, the solid sample was dissolved using acetonitrile/water (1/1) to make a solution with the concentration of 0.2 mg/mL. Sample solutions were analyzed by HPLC and solid samples were examined by XRPD.

Results of Solubility Test

The solubility of Compound FA, L-lysine salt and meglumine salt was tested in pH 1.2 and pH 6.8 buffer solutions at 30 min and 24 h. The remaining solid samples at 24 hours were analyzed by XRPD. HPLC results showed that the three samples tested were unstable in pH 1.2 buffer solution.

The solubility was calculated with the sum of impurities and major peak area. All solubility results were listed in Table 6. The two salts tested showed much higher solubility than Compound FA at 30 min and 24 hours. XRPD analysis show that L-lysine salt changed to amorphous, while crystallinity of Compound FA and meglumine salt became lower. Based on $^1$H NMR analysis, degradation occurred in pH 1.2 buffer and dissociation appeared in pH6.8 buffer.

TABLE 6

Solubility of Lysine Salt, Meglumine salt and Compound FA

| Sample | Media | Solubility at 30 min (mg/mL) | Solubility at 24 h (mg/mL) | XRPD patterns at 24 h |
| --- | --- | --- | --- | --- |
| Compound FA | pH 1.2 | 0.571 | 0.267 | Low crystallinity |
|  | pH 6.8 | 0.014 | 0.003 | Low crystallinity |
| Meglumine salt | pH 1.2 | 0.296 | 1.612 | No change |
|  | pH 6.8 | 0.020 | 0.017 | Low crystallinity |
| L-lysine salt | pH 1.2 | 0.387 | 1.343 | Amorphous |
|  | pH 6.8 | 0.017 | 0.019 | Amorphous |

The solubility in pH 1.2 was calculated with the sum of impurities and major peak area.

The solubility in pH1.2 was calculated with the sum of impurities and major peak area.

Results of Solid Stability Test

After storage at 40° C./75% RH for 8 days, solid stability test of Compound FA, L-lysine salt and meglumine salt was determined by HPLC and XRPD. HPLC results (Table 7) showed that no obvious degradation occurred, and the purity of the two tested salts was higher. XRPD patterns were not changed after storage at 40° C./75% RH for 8 days. Compound FA, L-lysine salt and meglumine salt were all physically and chemically stable at 40° C./75% RH for 8 days.

TABLE 7

Stability of Lysine Salt, Meglumine salt and Compound FA

| Sample | Purity at 0 day (Area %) | Purity at 8 days (Area %) |
| --- | --- | --- |
| Compound FA | 98.02 | 96.31 |
| Meglumine salt | 99.68 | 99.66 |
| L-lysine salt | 99.77 | 99.66 |

CONCLUSION

Crystalline L-lysine salt and meglumine salt (dihydrate and anhydride) were successfully prepared and characterized by $^1$H NMR, XRPD, DSC, TGA and DVS. By comparing solid state characteristics of each salt, L-lysine salt (Form A) and anhydrous meglumine salt (Form I) were selected for further evaluation along with free acid by solubility/solid stability testing.

In solubility testing, the two salts showed much higher solubility than Compound FA at 30 min and 24 hours. Compound FA and the salts were all degraded in pH 1.2 buffer. In solid stability evaluation, L-lysine salt and meglumine salt were both physically and chemically stable at 40° C./75% RH for 8 days. Their purity was higher than Compound FA.

Example 8. Preparing Tromethamine Salt of Compound FA, (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid Tromethamine salt was prepared in 2 conditions.

In one condition, 23.73 mg of Compound FA was dissolved in 500 μL of 0.1 M tromethamine/methanol solution with stirring at room temperature. Reacted for an hour at room temperature. Concentrated to dry, sticky product was obtained. Added 200 μL of ethyl acetate, the sticky sample was dissolved. Added 400 μL of n-heptane, and kept stirring overnight at room temperature. The sample was collected by filtration.

In another condition, 23.99 mg of Compound FA was dissolved in 800 μL of acetonitrile with stirring at 50° C. Added 50 μL of 1 M tromethamine/water solution and reacted at 50° C. for an hour. Cooled to room temperature and concentrated to about 300 solid sample appeared. The sample was obtained by filtration after stirring for about 1.75 hours.

Both samples were characterized by $^1$H NMR, XRPD, TGA, and DSC. XRPD and $^1$H NMR showed that crystalline salt with residual solvent was formed. For sample obtained in ethyl acetate/n-heptane, about 3.8% weight loss and endothermic peak at 117.4° C. was observed. For sample produced in ACN, 5.4% weight loss and 3 endothermic peaks were detected. Both of them were solvate. Representative XRPD and DSC spectra are shown in FIGS. 5A-5C.

Example 9. Preparing Choline Salt of Compound FA, (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid Acetonitrile and MTBE were used as solvent to prepare choline salt.

ACN Procedure: 23.76 mg of Compound FA was dissolved in 400 μL of acetonitrile with stirring at 50° C. Added 13.6 μL of 46% choline hydroxide 46% (W/W) aq. solution, and precipitation occurred few minutes later. Reacted for 30 min at 50° C. and collected the solid sample after cooled to room temperature.

MTBE Procedure: 24.00 mg of Compound FA was dissolved in 200 μL of MTBE with stirring at room temperature. Added 13.6 μL of 46% choline hydroxide 46% (W/W) aq. solution, and precipitation occurred after about 3 min. Reacted for 1 hour, the solid was obtained by filtration.

Both $^1$H NMR results showed that salt was formed with the ratio of n (Compound FA)/n (choline hydroxide)=1/1 and peaks of residual solvent was observed. Sample prepared in MTBE was amorphous confirmed by XRPD (FIG. 6A). The crystalline sample from acetonitrile was tested by TGA and DSC (FIG. 6B). There was about 6.4% weight loss and two endothermic peaks prior to decomposition. The sample was a solvate.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. An amine salt of (E)-3-(3,5-dichloro-4-((1R,3R)-2-(2-fluoro-2-methylpropyl)-3-methyl-2,3,4,9-tetrahydro-1H-pyrido[3,4-b]indol-1-yl)phenyl)acrylic acid ("Compound FA"), which is a lysine salt, arginine salt, tromethamine salt, choline salt, or ammonium salt, wherein the amine salt is in a crystalline form or an amorphous form, or a mixture thereof.

2. The amine salt of claim 1, which is an L-lysine salt of Compound FA.

3. The amine salt of claim 2, wherein the L-lysine salt of Compound FA is in Form A, characterized by an X-ray powder diffraction (XRPD) pattern having one or more of the following peaks: 10.2, 13.0, 19.4, 20.9, 22.2, 22.4, and 22.9 degrees 2 theta, ±0.2°.

4. The amine salt of claim 2, wherein the L-lysine salt of Compound FA is in Form A, characterized by an X-ray powder diffraction (XRPD) pattern having all of the following peaks: 10.2, 13.0, 19.4, 20.9, 22.2, 22.4, and 22.9 degrees 2 theta, ±0.2°.

5. The amine salt of claim 2, wherein the L-lysine salt of Compound FA is in Form A, characterized by an X-ray powder diffraction (XRPD) pattern having all of the following peaks: 4.2, 10.2, 11.1, 13.0, 13.3, 19.4, 20.9, 22.2, 22.4, 22.9, 24.6, and 31.7 degrees 2 theta, ±0.2°.

6. The amine salt of claim 2, wherein the L-lysine salt of Compound FA is in Form A, characterized by an XRPD pattern substantially the same as shown in FIG. 4A.

7. The amine salt of claim 1, which is a tromethamine salt of Compound FA.

8. The amine salt of claim 7, wherein the tromethamine salt of Compound FA is in a crystalline form.

9. The amine salt of claim 1, which is a choline salt of Compound FA.

10. The amine salt of claim 9, wherein the choline salt of Compound FA is in a crystalline form.

11. The amine salt of claim 1, which is an ammonium salt or an arginine salt of Compound FA.

12. A pharmaceutical composition comprising the amine salt of claim 1, and optionally a pharmaceutically acceptable excipient.

* * * * *